US009636065B2

(12) United States Patent
Borkar et al.

(10) Patent No.: US 9,636,065 B2
(45) Date of Patent: May 2, 2017

(54) DETECTING LEAKAGE FROM AN INTERNAL SURGICAL SITE

(71) Applicant: Empire Technology Development LLC, Wilmington, DE (US)

(72) Inventors: Prashant Borkar, Aurangabad (IN); Mangesh Patankar, Navi Mumbai (IN); Rahul Nair, Thiruvanahtra (IN); Cinish Puthiyedathu Varghese, Mannamkandam (IN)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 312 days.

(21) Appl. No.: 14/350,746

(22) PCT Filed: Sep. 27, 2013

(86) PCT No.: PCT/US2013/062431
§ 371 (c)(1),
(2) Date: Apr. 9, 2014

(87) PCT Pub. No.: WO2014/052908
PCT Pub. Date: Apr. 3, 2014

(65) Prior Publication Data
US 2015/0018855 A1    Jan. 15, 2015

(30) Foreign Application Priority Data
Sep. 29, 2012   (IN) .......................... 3069/DEL/2012

(51) Int. Cl.
*A61B 17/11*    (2006.01)
*A61B 5/00*    (2006.01)
(Continued)

(52) U.S. Cl.
CPC .......... *A61B 5/4833* (2013.01); *A61B 5/4851* (2013.01); *A61B 17/08* (2013.01);
(Continued)

(58) Field of Classification Search
CPC .................... A61B 17/08; A61B 17/11; A61B 2017/00243; A61B 2017/081;
(Continued)

(56) References Cited

U.S. PATENT DOCUMENTS 4,953,548 A    9/1990  Stoddard et al.
7,837,669 B2  11/2010  Dann et al.
(Continued)

FOREIGN PATENT DOCUMENTS

WO    2005/096954 A2    10/2005

OTHER PUBLICATIONS

Mrowczynski et al., "A Biodegradable Ring Enables Growth of the Native Tricuspid Annulus", Journal of Heart Valve Disease, vol. 20, Issue 2, Mar. 2011, pp. 205-215.
(Continued)

*Primary Examiner* — Eric Rosen
*Assistant Examiner* — George J Ulsh
(74) *Attorney, Agent, or Firm* — Maschoff Brennan

(57) ABSTRACT

A leakage detecting implant can detect leakage of body fluid from an incision, resection, or other internal surgical site in a subject. The leakage detecting implant can include: one or more biodegradable colorant members having a tissue-contacting inner surface and an opposite outer surface; a resilient member having an inner surface coupled to the outer surface of the one or more colorant members; and a cover member having a body with an internal chamber and an opening on a tissue-contacting side, the internal chamber containing the resilient member and at least a portion of the one or more biodegradable colorant members with the
(Continued)

tissue-contacting inner surface exposed through the opening, the cover member having an inner surface of the internal chamber coupled to an outer surface of the resilient member, the tissue-contacting side having one or more affixation surfaces adapted to be affixed to tissue of a subject.

36 Claims, 18 Drawing Sheets

(51) Int. Cl.
    *A61B 17/08*     (2006.01)
    *A61B 17/00*     (2006.01)
    *A61B 90/00*     (2016.01)

(52) U.S. Cl.
    CPC ........... *A61B 17/11* (2013.01); *A61B 17/1114* (2013.01); *A61B 2017/00243* (2013.01); *A61B 2017/00526* (2013.01); *A61B 2017/081* (2013.01); *A61B 2017/1103* (2013.01); *A61B 2017/1107* (2013.01); *A61B 2017/1132* (2013.01); *A61B 2090/0807* (2016.02); *A61B 2090/0809* (2016.02); *Y10T 29/49826* (2015.01)

(58) Field of Classification Search
    CPC .... A61B 2017/1103; A61B 2017/1107; A61B 2017/1132; A61B 2090/0807; A61B 2090/0809; A61B 17/1114; A61B 5/4833; A61B 5/4851; A61B 2017/00526; A61B 17/12; Y10T 29/49826; A61F 13/42
    USPC ........................................................ 606/154
    See application file for complete search history.

(56) References Cited

U.S. PATENT DOCUMENTS

| | | |
|---|---|---|
| 2001/0049557 A1 | 12/2001 | Chinn et al. |
| 2003/0114818 A1* | 6/2003 | Benecke ............... A61F 13/505 604/378 |
| 2004/0092892 A1 | 5/2004 | Kagan et al. |
| 2009/0157180 A1 | 6/2009 | Schraga |
| 2010/0010519 A1 | 1/2010 | Stopek et al. |
| 2011/0106035 A1* | 5/2011 | Arora ...................... A61L 15/56 604/367 |

OTHER PUBLICATIONS

International Search Report and Written Opinion of the International Searching Authority dated Dec. 30, 2013 as received in International Application No. PCT/US2013/062431.
Ovnat A., et al., "Early detection and treatment of a leaking gastrojejunostomy following gastric bypass.", Isr J Med Sci., 1986.
Anastomotic Leak Testing After Colorectal Resection. What Are the Data? Rocco Ricciardi, MD, MPH; Patricia L. Roberts, MD; Peter W. Marcello, MD; Jason F. Hall, MD; Thomas E. Read, MD; David J. Schoetz, MD., 2009.
Can intraluminal devices prevent or reduce colorectal anastomotic leakage: A review. Annelien N Morks, Klaas Havenga, Rutger J Ploeg, Oct. 28, 2011.
Development of a biosensor for early detection of anastomotic leak after bowel surgery. N. Hirst*, D. Jayne, P. Millner University of Leeds, UK. Jan. 22, 2014.
http://www.professionalequipment.com/bright-dyes-biodegradable-non-fluorescent-dye-tracers-industrial-blue-106002-01g/water-testing-accessories/, Apr. 9, 2014.

* cited by examiner

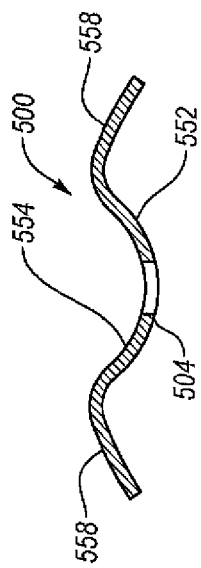
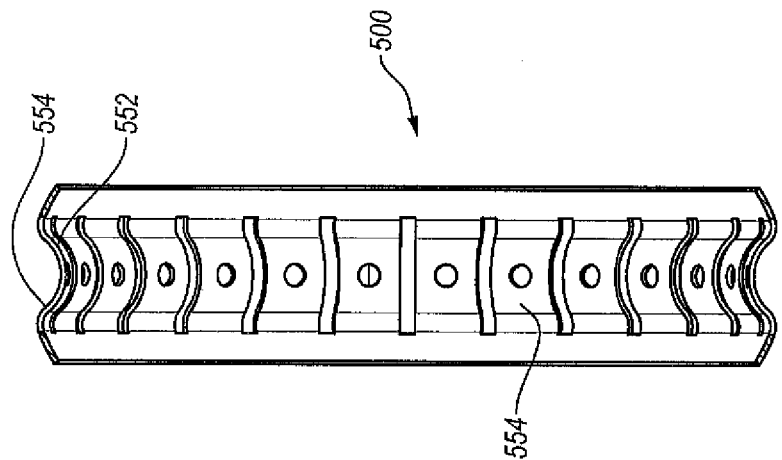
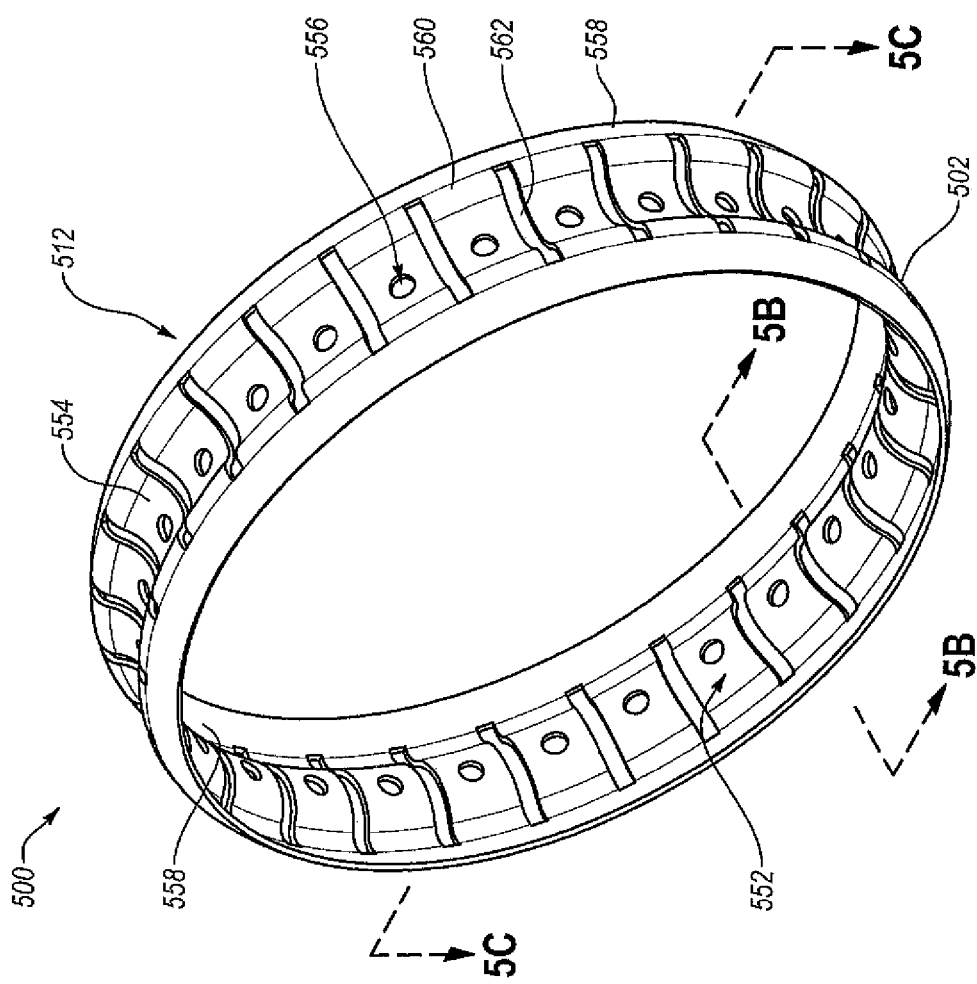
Fig. 5B
Fig. 5C
Fig. 5A

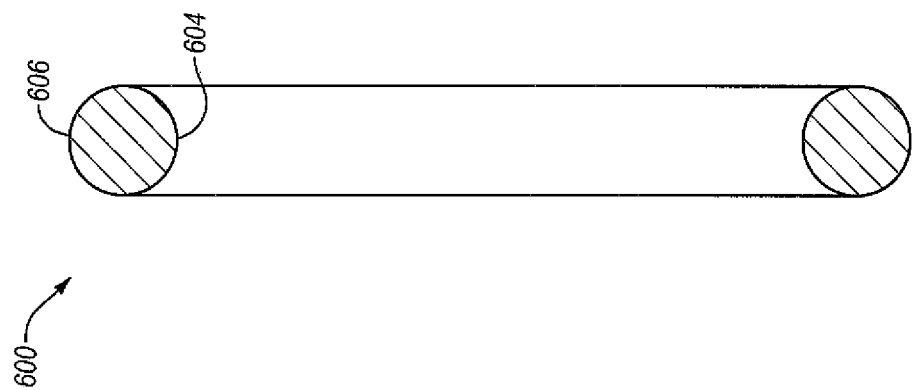
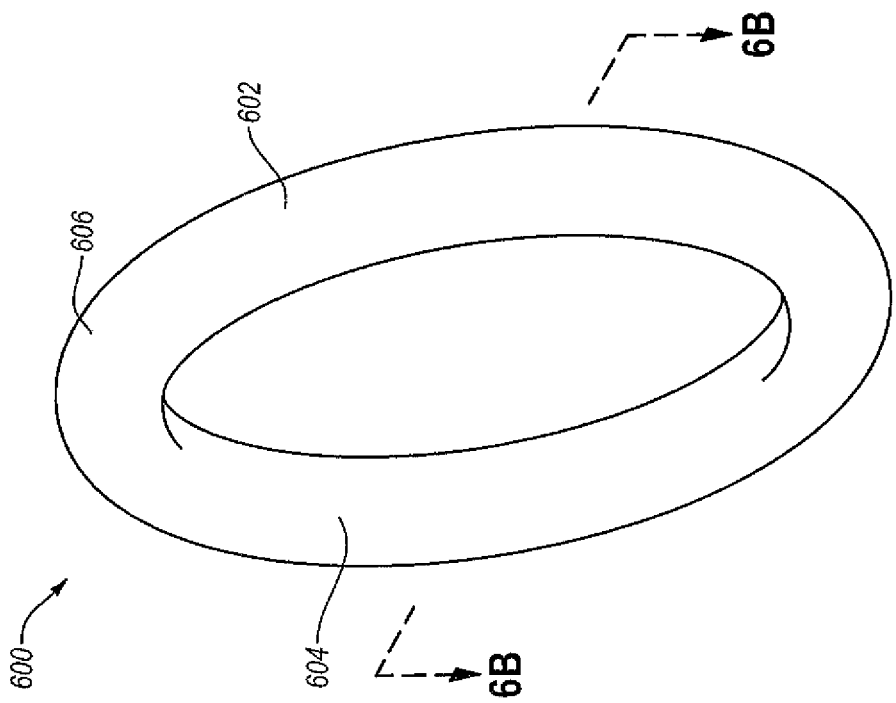

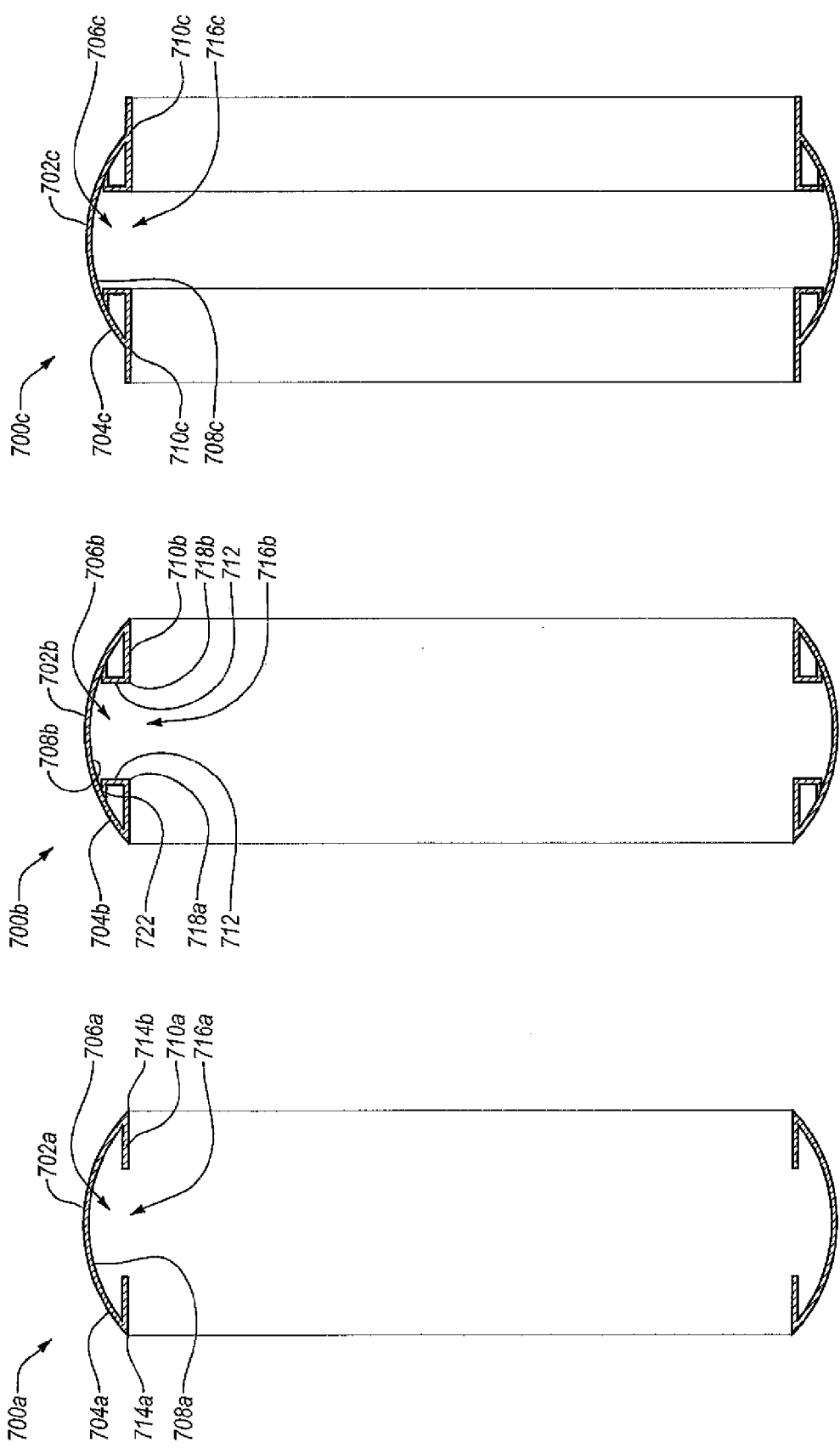

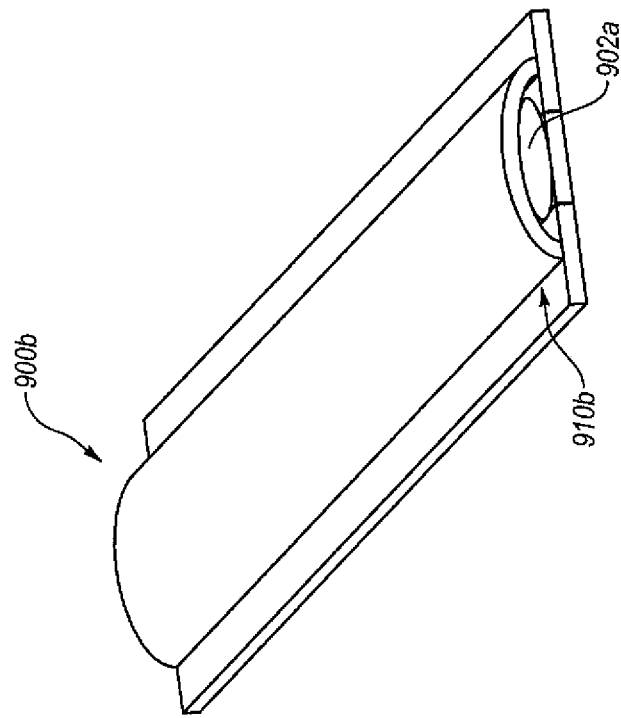
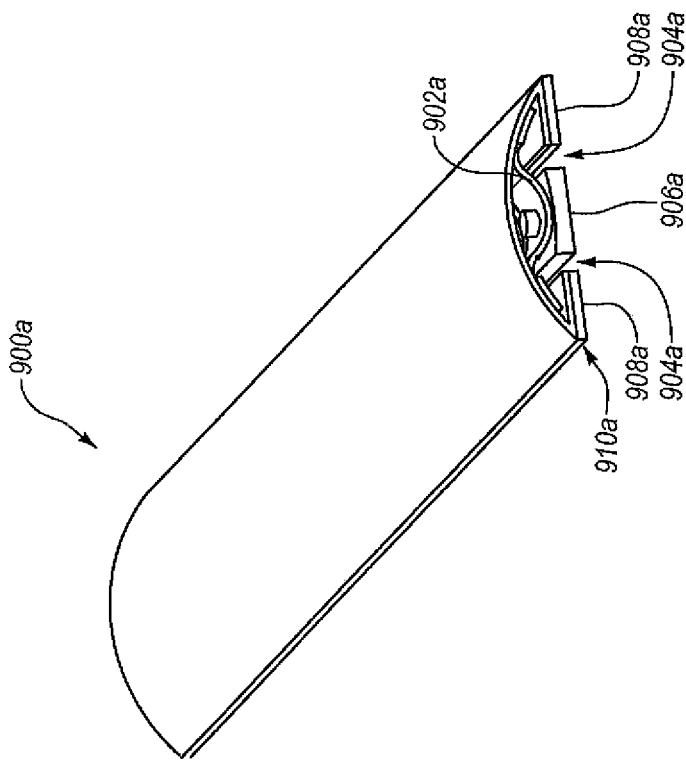

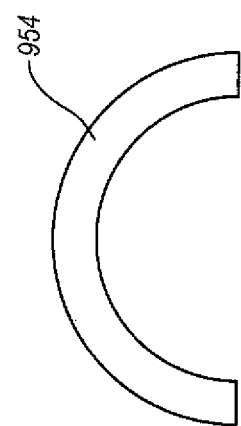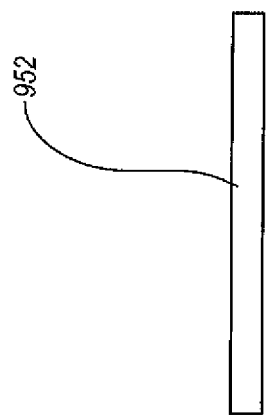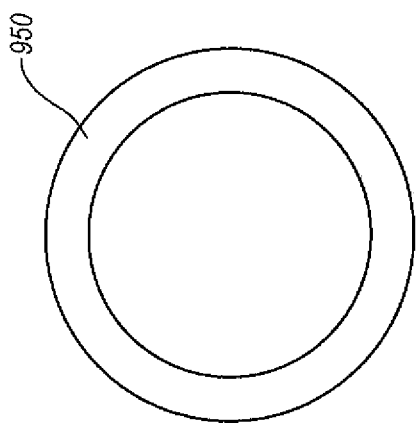
Fig. 9C

DETECTING LEAKAGE FROM AN INTERNAL SURGICAL SITE

CROSS-REFERENCE RELATED TO APPLICATIONS

The present Application is the U.S. National stage filing under 35 U.S.C § 371 of PCT Application No. PCT/US13/62431 filed on Sep. 27, 2013. This application also claims priority from an Indian Patent Application No. 3069/DEL/2012 filed on Sep. 29, 2012.

BACKGROUND

Surgical procedures can result in post-surgical complications that need to be addressed and rectified in order for the surgical patient to make a full and healthy recovery. The various possible complications of a surgical procedure can include a surgical site leaking or oozing blood of other body fluids, which can be life-threatening especially when the surgical site is inside the body at an internal organ or body lumen, such as the gastrointestinal ("GI") tract. While other complications, such as infection, can be problematic, many are often treatable or can be overcome without reopening the surgical site or having to perform a subsequent surgical procedure. However, blood or other body fluid leakage from an internal surgical site can go undetected until the leakage becomes life threatening and the surgical patent becomes extremely sick or even dies.

For example, colorectal anastomosis procedures can result in anastomotic leakage from the internal surgical site, which can cause severe heath complications and even death. One problem with anastomotic leakage from a colorectal surgical site is that the leak is internal and not visually detectable once the surgical patient has been closed up, and confirmation of such a leakage can require the original surgical site to be reopened and examined.

Accordingly, it can be difficult for a medical professional to determine whether or not an internal surgical site has a leakage. Often, surgical complications are monitored by assessing clinical symptoms, such as fever, breathing difficulties, neurologic irregularities, and sepsis. However, blood or other body fluid leakage from an internal surgical site may not present clinical symptoms for one or more weeks post-surgery. During the lag time after surgery and before clinical symptoms manifest, a surgical patient with an internal leakage may become extremely sick, incurable, and possibly die.

Major complications of a colorectal anastomosis can arise from the leakage being from the surgical site where two parts of the GI tract were put back together. In this type of internal surgical procedure, the chance of a leak can be substantial. Additionally, patients that have other health complications, such as elderly patients, diabetic patients, or cancer patients, can take longer to heal from a colorectal anastomosis and may be more susceptible to developing an anastomotic leak.

SUMMARY

In one embodiment, the present disclosure describes an implant that can include: one or more biodegradable colorant members having a tissue-contacting inner surface and an opposite outer surface; a resilient member having an inner surface coupled to the outer surface of the one or more colorant members; and a cover member having a body with an internal chamber and an opening on a tissue-contacting side, the internal chamber containing the resilient member and at least a portion of the one or more biodegradable colorant members with the tissue-contacting inner surface exposed through the opening, the cover member having an inner surface of the internal chamber coupled to an outer surface of the resilient member, the tissue-contacting side having one or more affixation surfaces adapted to be affixed to tissue of a subject.

In one embodiment, a method of detecting leakage from an internal surgical site can use the implant described herein. The method of detecting the leakage can include: affixing the implant having one or more biodegradable colorant members to the internal surgical site in a subject; allowing the biodegradable colorant to degrade at the surgical site; and determining whether color of the colorant member is leaking or otherwise flowing from the surgical site.

In one embodiment, the implant includes a shape of a ring, where the method can include: performing a surgical procedure to produce the surgical site, the surgical procedure resecting a portion of a GI tract of a subject, during the resection: separating a first portion of the GI tract from a second portion; placing the ring implant over an end of one of the first portion or second portion; ligating the first portion with the second portion, wherein the surgical site includes the ligation; placing the ring implant at the surgical site so that a portion of ring implant is at the first portion of the GI tract and a portion of the ring implant is at the second portion of the GI tract; and affixing the implant to the first portion and second portion of the GI tract such that the one or more biodegradable colorant members contact the ligation.

In one embodiment, a method of manufacturing an implant as described herein can include: preparing one or more biodegradable colorant members having a tissue-contacting inner surface and an opposite outer surface; preparing a resilient member having an inner surface; coupling the inner surface of the resilient member to the outer surface of the one or more biodegradable colorant members; preparing a cover member having a body with an internal chamber and an opening on a tissue-contacting side between one or more affixation surfaces adapted to be affixed to tissue of a subject; and inserting the coupled resilient member and one or more biodegradable colorant members into the internal chamber of the cover member such that the internal chamber contains the resilient member and at least a portion of each of the biodegradable colorant members with the tissue-contacting inner surface exposed through the opening, the cover member having an inner surface of the internal chamber coupled to an outer surface of the resilient member.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

In the drawings:

FIG. 5A includes a perspective view of a leaf spring resilient member of a leakage detecting implant;

FIG. 5B includes a cross-sectional view of a portion of the leaf spring resilient member of FIG. 5A;

FIG. 5C includes a front profile view of the leaf spring resilient member of FIG. 5A;

FIG. 6A includes a perspective view of a torus resilient member of a leakage detecting implant;

FIG. 6B includes a cutaway view of the torus resilient member of FIG. 6A;

FIG. 7A includes a cross-sectional view of cover members of a leakage detecting implant;

FIG. 7B includes a cross-sectional view of a cover member of a leakage detecting implant that has friction members for retaining the colorant members;

FIG. 7C includes a cross-sectional view of a cover member of a leakage detecting implant having extended tissue affixation flanges;

FIG. 9A includes a cutaway perspective view of a flat leakage detecting implant having a leaf spring resilient member;

FIG. 9B includes a cutaway perspective view of a flat leakage detecting implant having a torus resilient member;

FIG. 9C includes schematic representations of side profiles of leakage detecting implants;

DETAILED DESCRIPTION

Figure 1A:
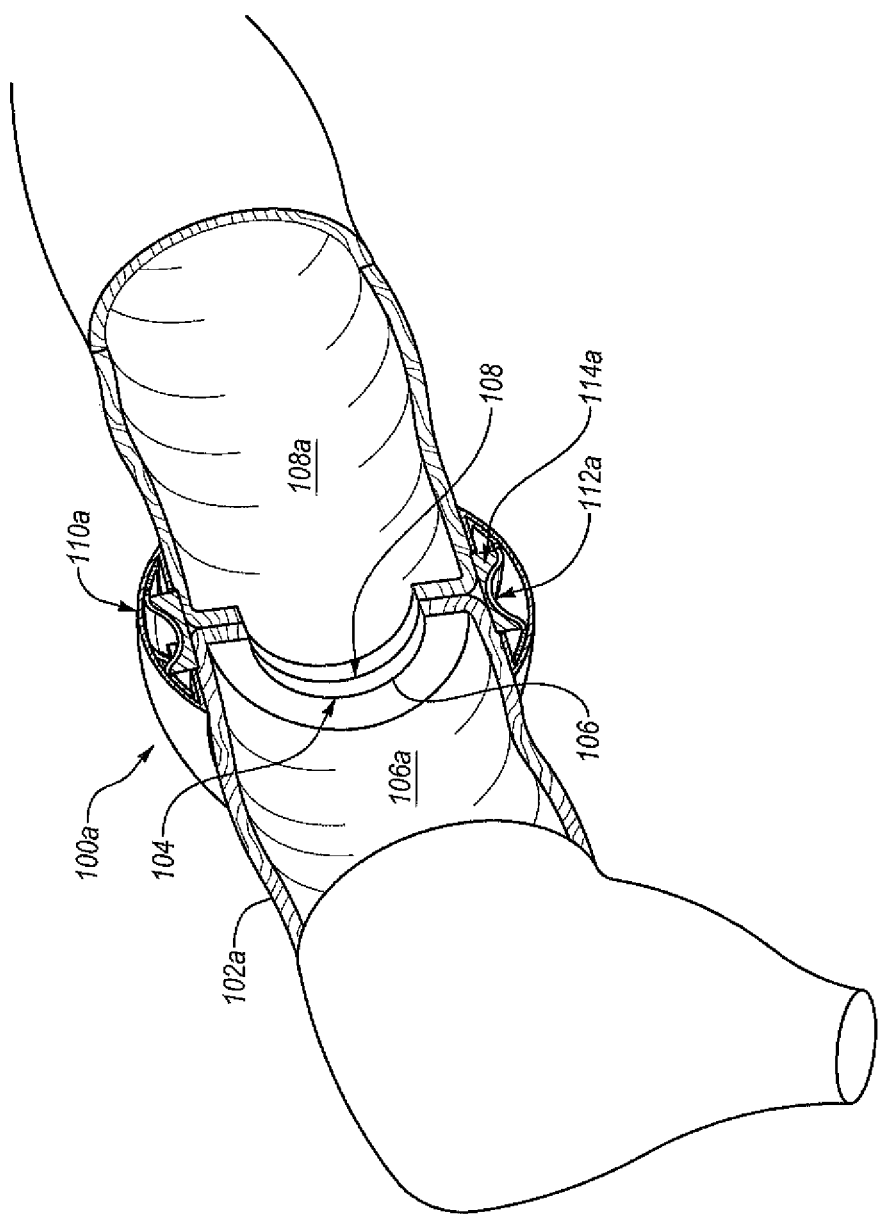
FIG. 1A includes a cross-sectional view of a leakage detecting implant implanted on a colon.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, a leakage detection implant can be implanted at an internal surgical site so that blood or other body fluid that leaks from the surgical site can be detected. The leakage detection implant can be used to detect an internal leakage without a subsequent surgery that reopens the surgical site. The leakage detection implant can be used at any location in the body to detect leakage from an internal organ, body lumen, or other tissue that is the subject of a surgical procedure. The leakage detection implant may also be used to detect leaks at internal malformations that have been repaired, such as at the site of a repaired fistula or other repaired malformation. While the leakage detection implant can be configured for use with any internal organ, body lumen, or tissue, some embodiments can be configured for use at a surgical site in the GI tract, such as at a colorectal anastomosis surgical site.

The leakage detection implant can be configured such that an internal leakage from a surgical site can be visually identified, such as with natural vision or with visualization via imaging equipment or devices. Accordingly, the leakage detection implant can include a leakage detection substance, such as a dye. The leakage detection substance can be a visible leakage detection substance or a non-visible leakage detection substance that is not visible to the naked eye. The leakage detection substance can be visible under normal light, UV light, IR light, or visible in response to light of any wavelength. Normal lighting or white light can be used for colored dyes used as leakage detection substances. In one example, a "black light" may be used to illuminate the leakage detection substance, such as a fluorescent or phosphorescent substance, for visualization. The non-visible leakage detection substance can be a reagent or dye that is detected by chemical reaction, combination of another substance, or by a device. For example, the leakage detection substance can be non-visible, but then become visible when reacted with a reagent. In another example, the leakage detection substance can be non-visible, but then become visible when combined with another substance in an immunoassay. In yet another example, the leakage detection substance can be radiopaque and visualized with a fluoroscopy device. In one aspect, the imaging can be with the naked eye from viewing excrement when the surgical site is in the GI tract. In another aspect, the imaging can be accomplished with devices or equipment configured for visual observation of internal organs or tissues. The devices or equipment for internal visual observation can include endoscopes or the like that can be inserted into the body through a natural body opening or incision. Also, the devices or equipment for internal visual observation can be configured for imaging through skin without an incision, such as X-ray, fluoroscopy, or the like. Accordingly, the leakage detection implant can include a biodegradable colorant member as the leakage detection substance that is degraded by blood or other body fluid so that the colorant flows away from the implant when contacted by a blood or other body fluid from a surgical site that is leaking.

In one embodiment, the leakage detection colorant can be a visual colorant that emits a color from red to violet (e.g., red, orange, yellow, green, blue, indigo, violet, and combinations other of and the like) so that the colorant can be seen with the naked eye. Examples of visual colorants can include dyes and pigments that are biocompatible. The visual colorant can be biocompatible so that the colorant itself does not cause any medical problem or complication at the surgical site, such as irritation or inflammation. The visual colorant can be suitable for an implant that is configured for implantation at a surgical site on the GI tract such that when blood or other body fluid leaks and contacts the visual colorant, the colorant will also flow through the leaking surgical site and into the GI tract. Once the colorant is in the GI tract, the surgical site leakage can be determined from visual analysis of the stool. The visual colorant may be visually distinguished from stool. Such a visual determination can be made by the surgical patient without any visualization devices or equipment.

In one embodiment, the leakage detection substance can be radiopaque such that blood or other body fluid that leaks from the surgical site can cause the radiopaque leakage detection substance to flow away from the implant into body space or into the organ that underwent a surgical procedure. A radiopaque imaging technique, such as X-ray or fluoroscopy, can be used to visualize the internal flow or distribution of the radiopaque leakage detection substance away from the implant. When the radiopaque leakage detection substance flows or is otherwise distributed around or away from the implant, or anywhere other than in the implant, the surgical site is likely to be leaking.

The leakage detection substance can be generally referred to herein as a colorant, and any reference to a colorant can include any of the leakage detection substances described herein or discovered, whether visible or non-visible or reactive or device-detectable, that can be used for leakage detection with the leakage detection device. Such detection of the colorant flowing or distributed from the implant by the surgical patient or by any medical professional can allow for early detection of leakage from an internal surgical site. Such leakage detection can occur before clinical systems arise or are detectable.

The colorant can be placed directly on the GI surgical site so that liquid leaking from the surgical site causes the colorant to particularize, liquefy or otherwise be capable of flowing. The colorant can pass from the implant and through the leaking surgical site and into the GI tract in an amount sufficient to color or tint the stool with the color of the colorant. Accordingly, blue is a color that is usually not present in stool, and thereby stool having the blue colorant can be easily distinguished from normal stool; however, other colors can be used, such as red, orange, yellow, green, indigo, violet and any other color that can be visually distinguished from natural stool color.

In one embodiment, a leakage detecting implant can include an outer cover member containing a resilient member and a colorant member. The colorant member can be provided in the leakage detecting implant as one or more biodegradable colorant members having a tissue-contacting inner surface and an opposite outer surface. The tissue-contacting inner surface of the colorant member can be flat or contoured to match contours of a tissue having the surgical site. Also, the tissue-contacting inner surface can be convex or concave, and can protrude from the outer cover member so as to be exposed to tissue when the implant is affixed to the tissue. The outer surface of each colorant member can have any shape or contouring, and may include a fastener member that can fasten the colorant member with the resilient member.

The resilient member can include an inner surface that faces and contacts each colorant member and an outer surface that faces and contacts the cover member such that the resilient member is positioned between and is capable of providing pressure to the cover member and each colorant member. As such, the resilient member can have an inner surface coupled to the outer surface of the each of the colorant members. The coupling between the resilient member and each colorant member can be via a coupling mechanism that can include a fastener member received by the resilient member. Also, the coupling between the resilient member and each colorant member can be a compression coupling where the resilient member pushes against the colorant member which in turn pushes against the tissue when implanted. An adhesive can also couple the colorant members to the resilient member. The resilient member or cover member can include friction members that friction couples the resilient member with each colorant member.

The cover member can have a body with an internal chamber and an opening on a tissue-contacting side that is opposite from an outer side. The internal chamber can contain the resilient member and at least a portion of each colorant member. Also, the tissue-contacting inner surface of each colorant member can be positioned so as to be exposed through the opening, and optionally protruding through the opening. The cover member can have an inner surface of the internal chamber that is coupled to the outer surface of the resilient member. The coupling between the cover member and resilient member can be by a fastener member, compression, or friction similar to the coupling between the resilient member and each colorant member. The cover member can also include a tissue-contacting side that has one or more affixation surfaces that are adapted to be affixed to tissue of a subject. That is, the affixation surfaces can include features or shapes that facilitate affixing the implant to the tissue at the surgical site.

The body of the cover member is adapted so that it can be affixed to tissue with seal. The seal between the body of the cover member and the tissue adjacent to the surgical site is sufficient to prevent body fluids entering into the internal chamber from the environment outside of the cover member. When affixed to tissue at a surgical site, the seal between the body of the cover member and the tissue can be sufficient so that fluids can enter from the surgical site through the opening. In one aspect, the direction that flowable colorant can be released from the cover member is through the opening, and the seal of the affixation surfaces prohibits the colorant from passing from the cover member. Accordingly, the cover member can have a fluid tight seal with the tissue at the affixation surfaces.

FIG. 1A includes a cross-sectional view of a leakage detecting implant 100a implanted on a colon 102a, arranged in accordance with at least some embodiments described herein. The implant 100a is shown to include a cover member 110a containing a resilient member 112a and colorant member 114a. The colon 102a is shown to have a surgical site 104, such as an anastomotic site, that includes a first tissue edge 106 coupled to a second tissue edge 108, where the coupling between the first tissue edge 106 and second tissue edge 108 can be by any surgical technique. The surgical site 104 is shown to be from a ligation of two tissue portions 106a, 108a. While the implant 100a is shown in a cross-sectional view around a circumferential surgical site 104, the implant 100a can extend across the surgical site and be affixed to both the two tissue portions 106a, 108a. Also, the implant 100a can be circular so as to fit around the colon 102a, or it can be "C" shaped and fit around a portion of the colon or other organ. Other shapes and configurations can be used as described herein.

Figure 1B:
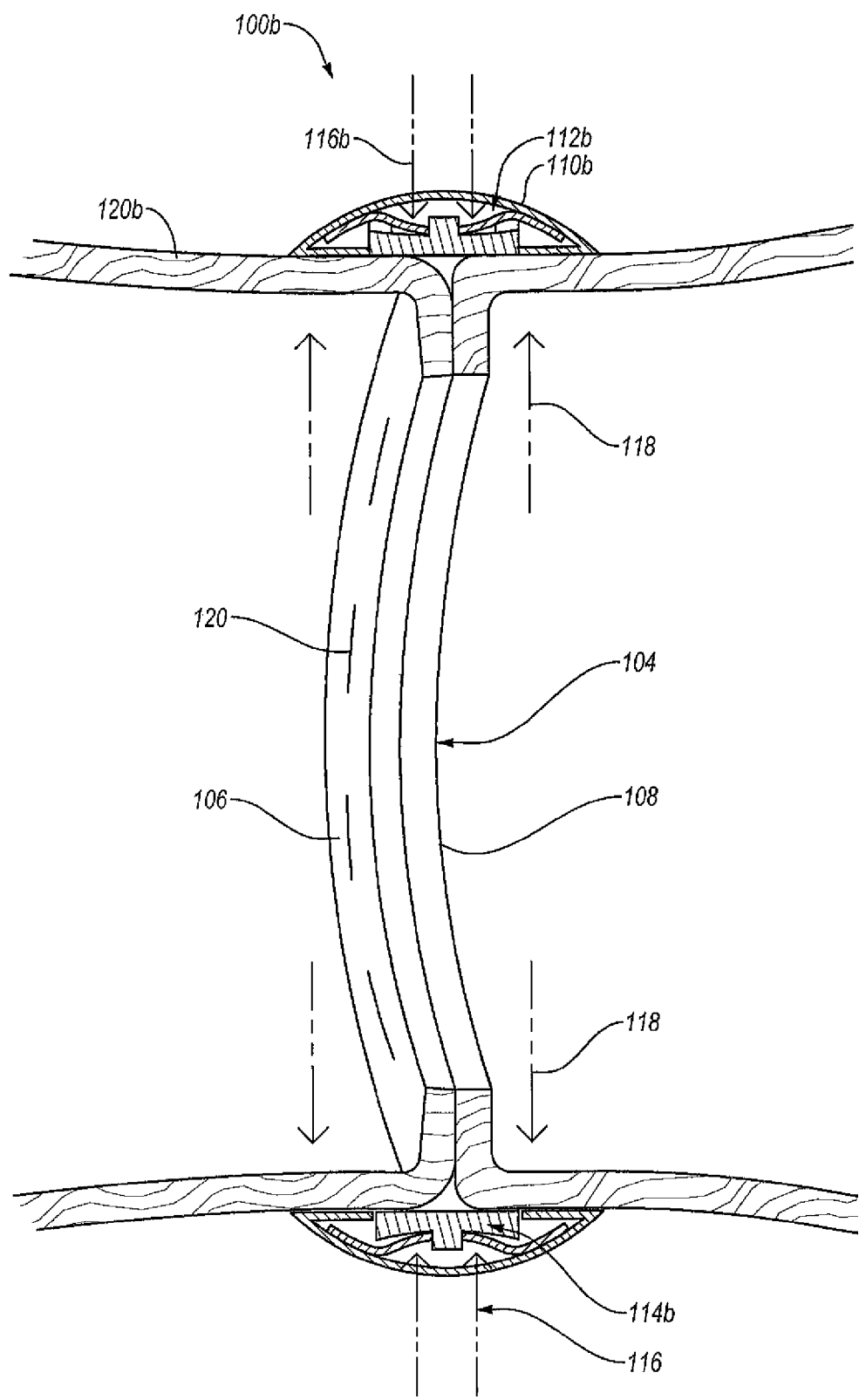
FIG. 1B includes a cross-sectional view of a leakage detecting implant implanted on a body lumen.

FIG. 1B includes a cross-sectional view of a leakage detecting implant 100b implanted on a body lumen 102b, arranged in accordance with at least some embodiments described herein. The implant 100b is shown to include a cover member 110b containing a resilient member 112b and colorant member 114b. The body lumen 102b can be any body lumen, and is shown to have a surgical site 104 that includes a first tissue edge 106 coupled to a second tissue edge 108 via sutures 120. However, the coupling between the first tissue edge 106 and second tissue edge 108 can be by any surgical technique. The resilient member 112b is shown in a strained state such that it presses against the cover member 110b and colorant member 114b so that pressure pushes the colorant member 114b against the surgical site 104, where the arrows 116 show the pressure applied by the resilient member 112b to the colorant member 114b. Also, the body lumen 102b can be resilient to also apply a counter pressure to the colorant member 114b, where arrows 118 show the counter pressure. Often, a body lumen 102b will include flowing fluids that can apply the counter pressure to the colorant member 114b. If the body lumen 102b is a blood vessel, the counter pressure can pulse along with the heartbeat. If the body lumen is an air passageway, breathing can cause the counter pressure to be cyclic.

Figure 1C:
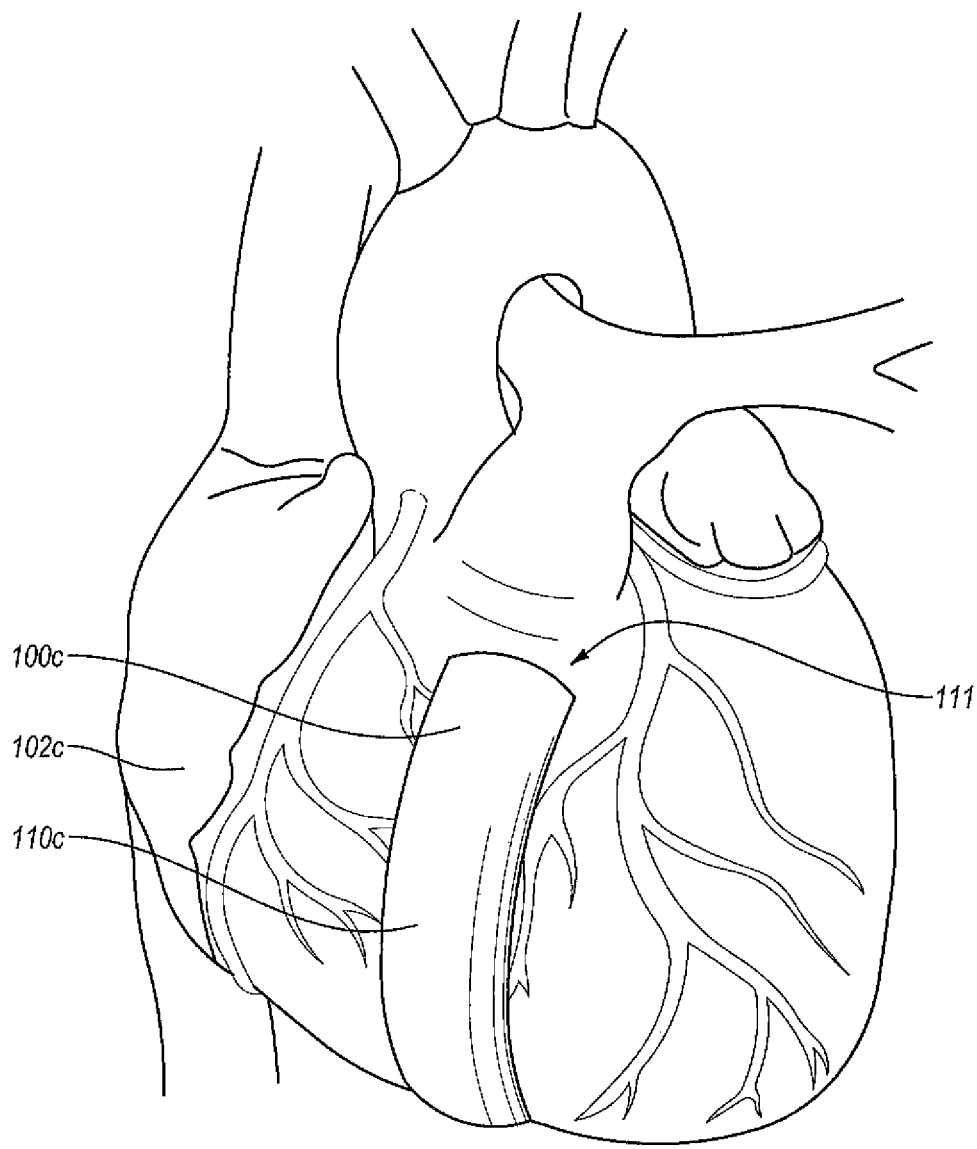
FIG. 1C includes an environmental view of a leakage detecting implant implanted on a body organ.

FIG. 1C includes an environmental view of a leakage detecting implant 100c implanted on a body organ 102c, arranged in accordance with at least some embodiments described herein. The implant 100c is shown to include a cover member 110c, which contains the resilient member (not shown) and colorant member (not shown). The cover member 110c includes a sealed end 111 that keeps body fluids from accessing the colorant member. The body organ 102c can be any body organ and is shown as a heart that has surgical site (not shown) under the implant 100c.

Figure 1D:
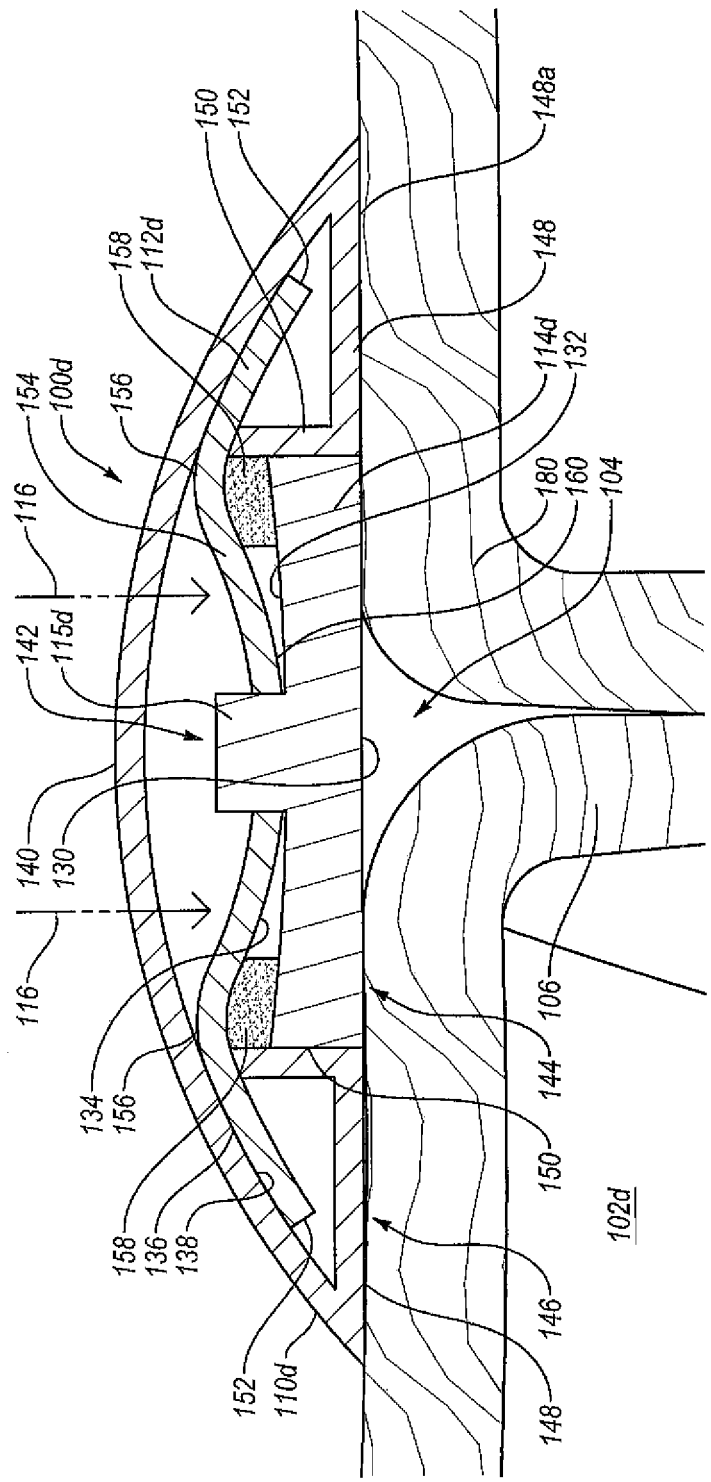
FIG. 1D includes a cross-sectional view of a schematic representation of a leakage detecting implant implanted at a surgical site of a tissue.

FIG. 1D includes a cross-sectional view of a schematic representation of a leakage detecting implant 100d implanted at a surgical site 104 of a tissue 102d, arranged in accordance with at least some embodiments described herein. The implant 100d can include a cover member 110d, a resilient member 112d, and one or more biodegradable colorant members 114d. Each colorant member 114d can have a tissue-contacting inner surface 130 and an opposite outer surface 132.

The resilient member 112d can be a unitary member that can be included within the cover member 110d adjacent to the one or more biodegradable colorant members 114d. The resilient member 112d is configured as a leaf spring and has an inner surface 134 coupled to the outer surface 132 of the one or more colorant members 114a. The resilient member 112d also includes an outer surface 136 that is coupled with an inner surface 138 of the cover member 110d.

The cover member 110d has a body 140 with an internal chamber 142 that has an opening 144 on a tissue-contacting side 146. The internal chamber 142 is dimensioned to contain the resilient member 112d and at least a portion of the one or more biodegradable colorant members 114d. However, the positioning of the colorant members 114d allows for the tissue-contacting inner surface 130 to be exposed through the opening 144. The cover member 110d also has an inner surface 138 of the internal chamber 142 coupled to an outer surface 136 of the resilient member 112d. The tissue-contacting side 146 of the cover member 110d has one or more affixation surfaces 148 adapted to be affixed to tissue 102d of a subject, such as an animal like a human, dog, cat, horse, cow, or the like, either domestic or wild. The affixation surfaces 148 can be sealed against a tissue.

In one embodiment, the cover member 110d can be connected to the resilient member 112d by a joint obtained from glue or welding. The connection between the cover member 110d and resilient member 112d maintains their relative positions. The position of the resilient member 112d can be held such that the colorant member 114d which is attached to resilient member 112d can remain centered or at its desired position with respect to the opening of the cover member.

The cover member 110d can also include friction members 150 that are opposite of the affixation surfaces 148, and located within the internal chamber 142 and positioned adjacent to the colorant members 114d. The friction members 150 can be spaced apart and dimensioned so as to receive the colorant members 114d therebetween so as to hold colorant members 114d with some friction.

The cover member 110d can be rigid so that it does not deform by the resilient member 112d pushing against its inner surface 138. Here, the resilient member 112d has a relaxed state that is narrower than the illustrated strained state, where the resilient member 112d is strained and trying to revert back to the narrowed relaxed state. As the resilient member 112d tries to narrow toward the relaxed state, pressure can be applied to both the inner surface 138 of the cover member 110d and the outer surface 132 of the colorant member 114d. Here, lateral wings 152 of the resilient member 112b extend from a "U" shaped center leaf spring 154 of the resilient member 112d, so that the overall shape is a stretched "M" shape in the strained state and a compressed or narrowed "M" shape in the relaxed shape. When trending toward the relaxed shape, the "U" shaped inner leaf spring 154 pushed downward onto the colorant member 114d.

The resilient member 112d can include shoulders 156 where the body bends between the lateral wings 152 and "U" shaped center leaf spring 154, where the shoulders 156 press against the cover member 110d to provide leverage for the pressure applied to the colorant member 114d. Accordingly, bumpers 158 can help hold the shoulders 156 against the cover member 110d or at least provide a cushion between the shoulders 156 and the colorant member 114d. The bumpers 158 may also be resilient and spring-like so as to expand as the colorant member 114d degrades and shrinks during the process of the resilient member 112 trending toward the relaxed and narrower state.

Additionally, while the colorant members can have various shapes as described in more detail below with respect to FIGS. 4A-4F, FIG. 1D shows the outer surface 132 having a recess 160 that receives the "U" shaped center leaf spring 154 of the resilient member 112d. The recess 160 can include the colorant fastener 115d extending therefrom so as to be received in the resilient member 112d.

Additionally, the implant 110d can be configured such that the tissue-contacting inner surface 130 of the colorant member 114d is substantially planar with the affixation surfaces 148. These surfaces can be planar by design when in the strained or relaxed state. When in the strained state, the cover member 110d can include a member (not shown) that holds the colorant member 114d planar with the affixation surfaces 148. Also, the opening 144 of the cover member 110d can be dimensioned smaller than the colorant member 114d so that the entire colorant member 114d is retained within the chamber 142. The affixation surfaces 148 may also be included on affixation flanges 148a that project inwardly from the cover member 110a so as to hold the colorant member 114d within the chamber 142.

Figure 2B:
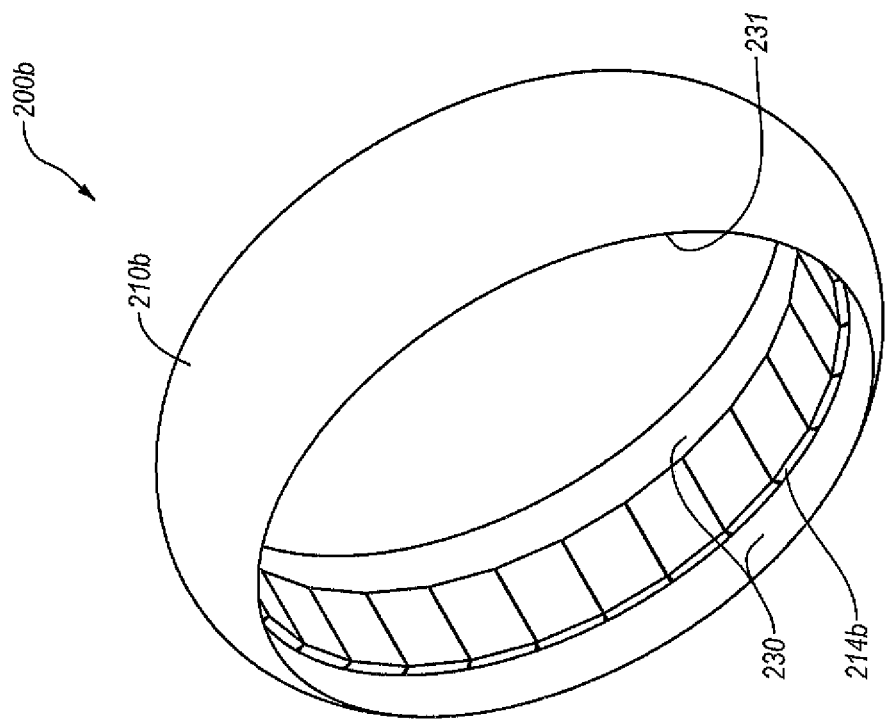
FIG. 2B includes a perspective view of a schematic representation of a continuous leakage detecting implant.
Figure 2A:
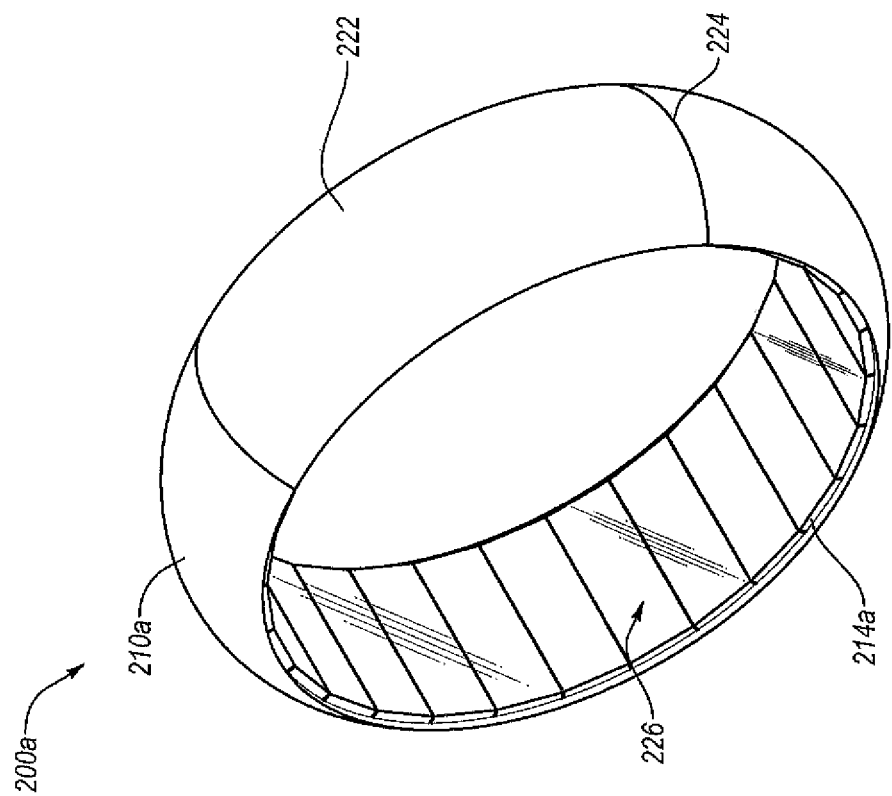
FIG. 2A includes a perspective view of a schematic representation of a sectional leakage detecting implant.

FIG. 2A includes a perspective view of a schematic representation of a sectional leakage detecting implant 200a, arranged in accordance with at least some embodiments described herein. The implant 200a is shown to include a cover member 210a, a plurality of colorant members 214a, and a peelable liner 226 on the tissue contacting-inner surface of the colorant members 214a. The cover member 210a is shown to be a sectional member with a plurality of sections 222 connected together at seams 224. The sections 222 and seams 224 can be useful for preparing the annular shaped cover member 210 so that the individual sections 222 can be prepared and then coupled together at the seams 224. While a number of sections 222 and seams 224 are shown, any number from 1 to any integer can be used. The colorant members 214a can be squared briquettes that are placed adjacent to each other so as to form an annular tissue-contacting inner surface. Also, the colorant members 214a can be adhered to a peelable liner 226, where the peelable liner 226 can be peeled so as to expose the tissue contacting inner surface.

FIG. 2B includes a perspective view of a schematic representation of a continuous leakage detecting implant 200b, arranged in accordance with at least some embodiments described herein. The implant 200b is shown to include a continuous cover member 210b, a plurality of colorant members 214b, and wide affixation surfaces 230 on each side of the colorant members 214b. Here, the cover member 210b is a continuous ring or annular shape without sections. Also, the cover member 210b is shown to include the wide affixation surfaces 230. The affixation surfaces 230 can be substantially flat and extend from an edge 231 of the cover member 210b toward the colorant members 214b.

Figure 2C:
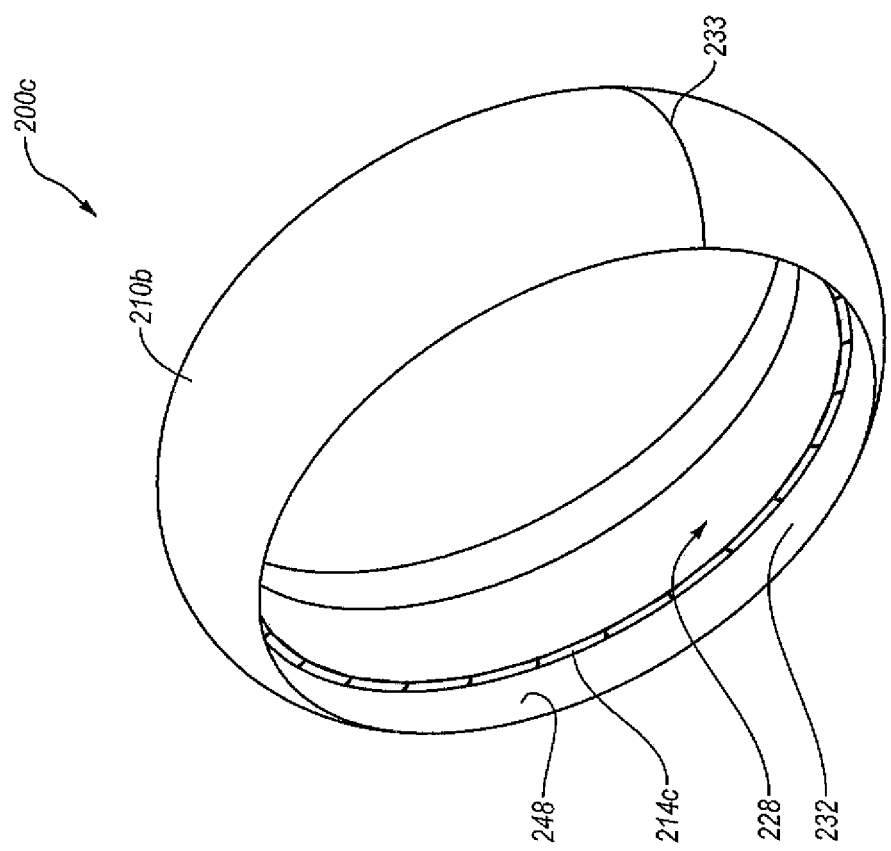
FIG. 2C includes a perspective view of a schematic representation of a clamp leakage detecting implant.

FIG. 2C includes a perspective view of a schematic representation of a clamp leakage detecting implant 200c, arranged in accordance with at least some embodiments described herein. The implant 200c is shown to include a cover member 210c, flanges 232, a plurality of colorant members 214c, and a dissolvable liner 228. The implant 200c is configured as a clamp with a break 233 that allows the implant 200c to be separated from the annular shape as shown to a "C" shape. For example, the implant 200c can be in the natural annular ring shape prior to use, and then opened at the break 233 to form a "C" shape before being slipped over the surgical site at a body lumen or other body organ before being released and allowed to resiliently move back to the natural annular ring shape. When the surgical site is at a body lumen, the implant 200c can resiliently move back to the annular ring shape upon implantation. When the surgical site is an organ, the implant 200c can stay in the "C" shape with pressure applied to the organ. The dissolvable liner 228 can be adhered to the colorant members 214c with an adhesive, and can be retained on the colorant members 214c during and after implantation. After implantation, the dissolvable liner 228 can dissolve so that the tissue-contacting inner surface of the colorant members 214c can contact the tissue at the surgical site.

The flanges 232 can be integrated or affixed to the cover member 210c. The flanges 232 can include the affixation surfaces 248 that can be used to affix and seal the implant 200c to a tissue. The flanges 232 having the affixation surfaces 248 can be of any thickness to allow for surgical staples, sutures, and surgical adhesive to affix the implant 200c to the tissue around the surgical site. Also, the width of the affixation surfaces 248 can be sufficient to extend in directions orthogonal to the surgical site over tissue adjacent to the surgical site for a secure fit.

Figure 3B:
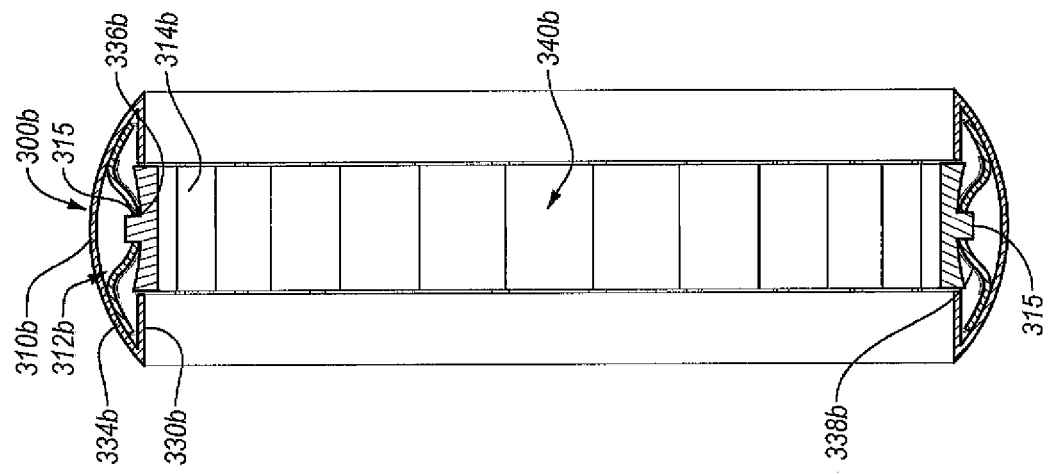
FIG. 3B includes a cutaway view of a leakage detecting implant.
Figure 3A:
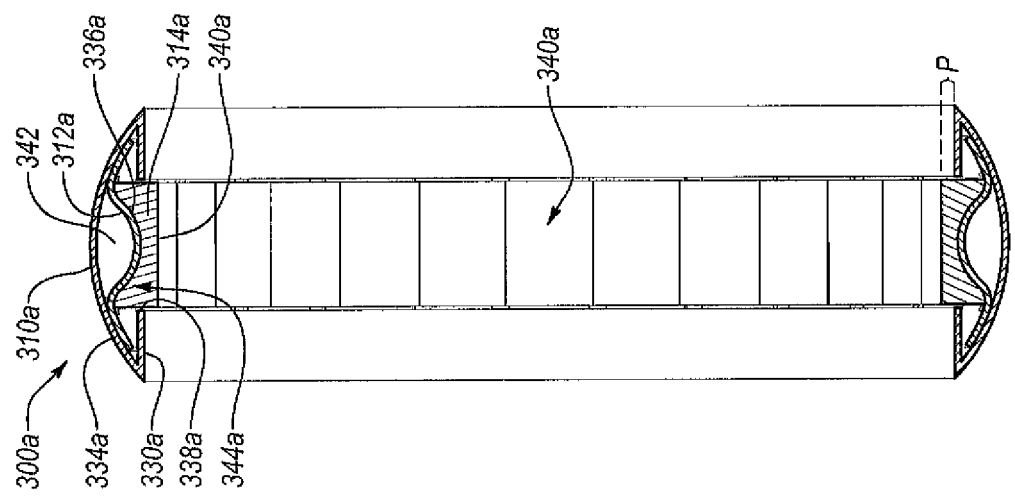
FIG. 3A includes a cutaway view of a leakage detecting implant.

FIG. 3A includes a cutaway view of a leakage detecting implant 300a, arranged in accordance with at least some embodiments described herein. The implant 300a is shown to include a cover member 310a housing a resilient member 312a, and at least a portion of the colorant member 314a. The cover member 310a is shaped similar to a "D" shape with an opening 344a in the flat side. The cover member 310 includes an internal chamber 342 that houses the resilient member 312a and a portion of the colorant member 314a. The cover member 310a is coupled to the resilient member 312a at a coupling 334a, which can be by a mechanical, weld, adhesive, or compression coupling. The resilient member 312a is configured as a leaf spring that has a "U" shape in the relaxed state, and has a straight or less bent shape when in the strained state such that the leaf spring trends from the shape shown to a narrower "U" shape as the colorant member 314a degrades. The resilient member 312a can be coupled to the colorant member 314a at a coupling 336a by an adhesive, or they can be coupled together by compression. Also, the cover member 310a and colorant member 314a can be coupled together at a friction coupling 338a that allows the colorant member 314a to move into and/or out from the internal chamber 342 with friction. As shown, the colorant member 314a extends from the internal chamber 342 through the opening 344a so that a portion of dimension P extends past the affixation surfaces 330a prior to implantation. Upon implantation, the tissue-contacting surface 340a is pushed toward and optionally into the internal chamber 342 so as to increase the strain state of the resilient member 312a and so that the tissue-contacting surface 340a is substantially planar with the affixation surfaces 330a. In some instances, the tissue-contacting surface 340a can apply pressure to the surgical site, and may even indent the tissue to a depth of up to or about 2 mm. While the resilient member 312a is shown as a thin leaf spring, it could also be in the form of a flattened cross-sectional profile torus shape in the strained state that is resilient and trends to a circular cross-sectional profile torus shape in the relaxed shape.

FIG. 3B includes a cutaway view of a leakage detecting implant 300b, arranged in accordance with at least some embodiments described herein. The implant 300b includes a cover member 310b, resilient member 312b, a plurality of colorant members 314b, and colorant fastener 315. The cover member 310b is coupled to the resilient member 312b via a coupling 334b similar to the couplings described above. The resilient member 312b is coupled with each colorant member via a coupling 336b, which is shown to include the colorant fastener 315 received by the resilient member 312b. Here, the resilient member 312b is a unitary member shown in a cross-sectional view receiving the colorant fastener 315 therethrough. A friction coupling 338b can couple the cover member 310b with the colorant member 314b. Also shown are the affixation surfaces 330b that extend laterally from the colorant members 314b to the external surface of the cover member 310b. The tissue-contacting surfaces 340b of the colorant members can extend from the cover member 310b and past the affixation surfaces 330b in a relaxed state and be planar with the affixation surfaces 330b when implanted and in the strained state.

Figure 4B:
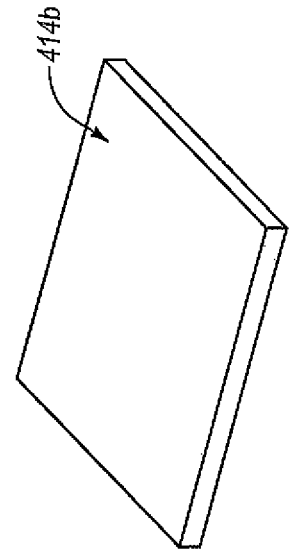
FIGS. 4A-4F include various views of schematic representations of biodegradable colorant members.
Figure 4D:
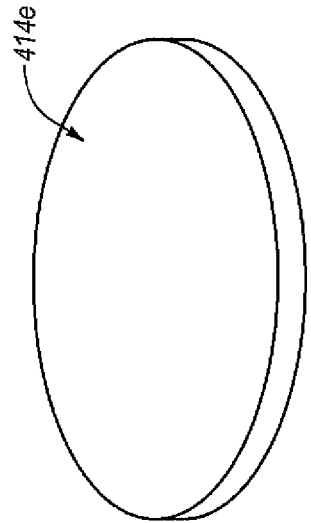
Figure 4A:
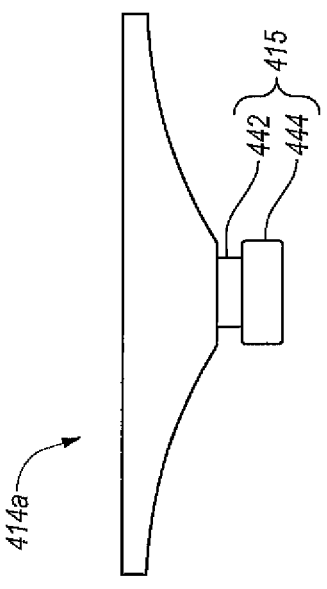
Figure 4C:
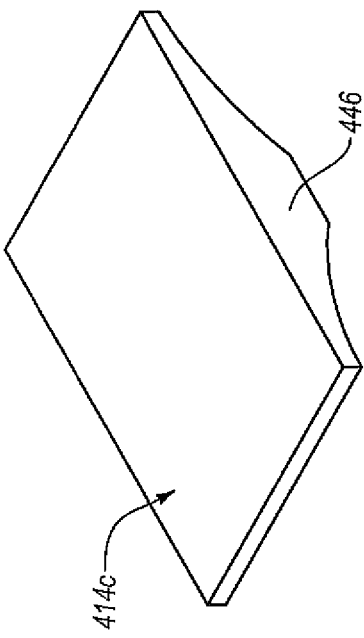

FIGS. 4A-4F include various views of schematic representations of biodegradable colorant members, arranged in accordance with at least some embodiments described herein. FIG. 4A shows a colorant member 414a having a body with a tapered potion that has a fastener member 415. The fastener member 415 includes a stem 442 and a cap 444, which can be received through a hole 556 in a resilient member 512 as described in more detail in connection with FIG. 5A. FIG. 4B shows a colorant member 414b in the shape of a briquette having in a square cross-sectional profile and a thin height. FIG. 4C shows a colorant member 414c having the shape of the body of FIG. 4A without the stem 442 and cap 444, where the tapered portion can abut with the resilient member. FIG. 4D shows a colorant member 414d having a circular cross-sectional profile and a thin height.

Figure 4E:
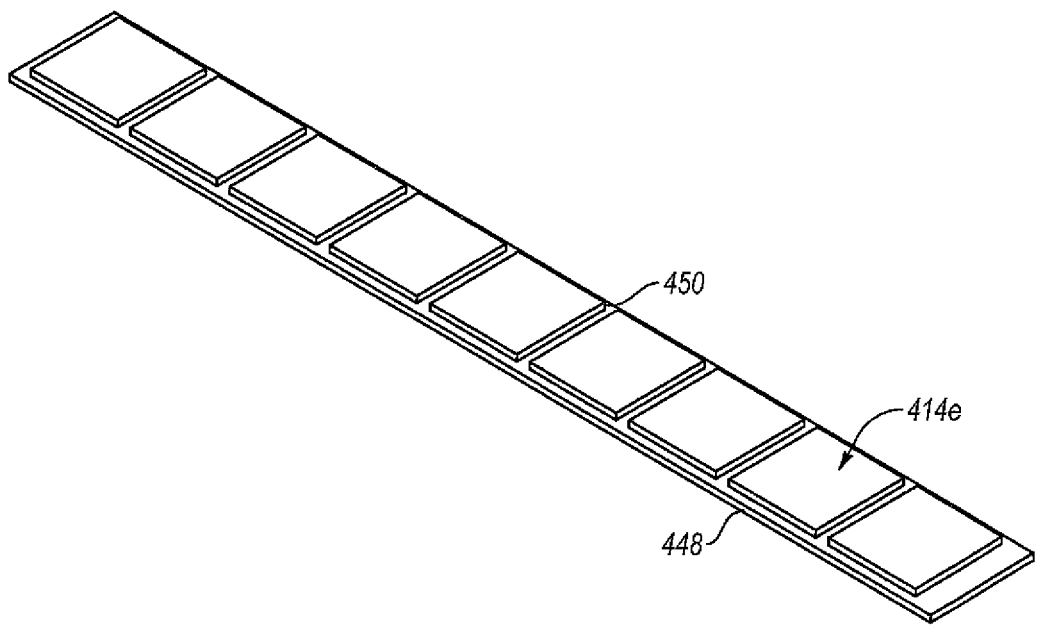

FIG. 4E shows a plurality of colorant members 414e attached to liner 448, where the liner 448 can be the dissolvable liner or peelable liner. While gaps 450 are shown between each of the colorant members 414e, the colorant members 414e can be adjacent and touching. Also, the liner 448 may be a pressure liner that is on the outer side opposite of the tissue-contacting surface, where the pressure liner can distribute pressure from the resilient member to the colorant members 414e, which can distribute the pressure across the entire surface area rather than a small contact area. The distribution of pressure can inhibit the colorant members 414e from cracking or breaking.

Figure 4F:
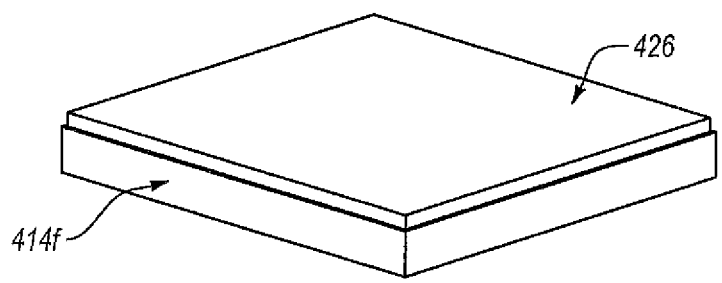

FIG. 4F shows the colorant member 414f having a dissolvable liner 426 on a tissue-contacting surface. The liner 426 can have a dimension from about 25 to about 100 microns, or from about 30 microns to about 75 microns, or from about 40 microns to about 60 microns, or about 50 microns. The width, length, or dimension of the liner 426 can be the same as the colorant member 414f. The liner 426 can be applied to the colorant member 414f during manufacture similar to application of a sticker, where the liner can include an adhesive, such as a pressure sensitive adhesive. The liner 426 can be prepared from poly(lactic acid), POLYOX™ (e.g., a anon-ionic poly(ethylene oxide) polymer), polycaprolactone, or the like.

The colorant members can have various configurations and compositions and still function as described herein. In one aspect, the colorant members include a biocompatible colorant so that the colorant does not cause a toxic reaction if leaked into the body. Also, the colorant can be edible so that does not cause GI tract complications when it passes through the surgical site and into the GI tract, such as at the colon. The colorant can be a food dye. In another aspect, the biodegradable colorant members can be selected from biodegradable solids, biodegradable aggregated particles, colored sheets, colored paper, sustained release members, biodegradable shell and colorant core members, and liquids or gels or powders in a biodegradable package. In fact, any format that is biodegradable and capable of being packaged in the implant and used as described herein would be suitable. In one aspect, the colorant members can include a colorant that is visibly distinguishable from stool.

In one embodiment, the colorant members can include a fastener member that couples the colorant members with the resilient member. Such a fastener member can be reviewed in FIG. 4A. However, the fastener member for a colorant member can have other configurations that allow for coupling with the fastener member, such as any fastener that can be inserted, threaded, snapped, or otherwise coupled with the resilient member. In one example, the fastener member can include a protrusion that is inserted into or through the resilient member. In another example, the protrusion can include a hook, barb, tine, stem and head, or the like.

In one embodiment, the colorant members can have a suitable amount of colorant so as to be visually observable as described herein. This can include the colorant members having at least about 0.4 g or 0.4 mL of total colorant for the implant, or the total colorant can be about 0.1 g or mL to about 1 g or mL, about 0.25 g or mL to about 0.75 g or mL, or about 0.5 g or mL. However, other amounts or volumes of colorant can be used. Also, the biodegradable colorant members can include a volume of about 0.1 mL to about 10 mL, from about 0.5 mL to about 5 mL, from about 1 to about 2 mL, or about 1.5 mL.

For example, the colorant members can include colorant at an average of 0.4 to 0.5 grams (e.g., compressed to a volume of 0.4 mL to 0.5 mL) when the implant is configured for a resected colon. By including an additional 0.5 to 1 mL as a design factor, the average colorant can range from 1 mL to 2 mL. Since extra colorant is inexpensive and safe, it will not harm any part of the body or cause a toxic response. The average colon size is four feet long with a with a width of 2 inches in most parts with a tissue thickness of 2 mm, the surgical site (e.g., anastomosis site) may have approximately 7 mm to 8 mm of area on each side of the incision for stitching. By considering the dimensions of the anastomosis site, the amount of colorant can be estimated.

Additionally, the colorant members can include a thickness of about 10 microns to about 1 cm, from about 25 microns to about 5 mm, from about 50 microns to about 2.5 mm, or from about 100 microns to about 1 mm, or about 500 microns. Furthermore, the colorant members can include a width or dimension that is orthogonal to thickness at from about 1 mm to about 50 mm, from about 4 mm to about 30 mm, from about 6 mm to about 20 mm, or from about 8 mm to about 12 mm.

In one example, each colorant member can include: a thickness that ranges from 100 microns to 1 mm; a dimension (e.g., orthogonal to thickness) of about 8 mm to about 12 mm; and the combination of the colorant members can form a ring having a diameter of about 48 mm. Generally, an anastomosis site can have approximately 7 mm to 8 mm of area for stitching, and the width 8 mm to 12 mm is suitable to extend across the anastomosis site.

The colorant members can have various formulations that are degradable. While solid bars that can disintegrate or packets that can release colorant powder are examples, the colorant member may also be a colored paper. That is, biodegradable paper can be used as a medium for holding the colorant. In another aspect, the colorant can have agglomerated colorant particles that are coated with a biodegradable coating that will dissolve when in contact with blood of other body fluids. The aggregated particles can be in a tablet form from being pressed with or without a binder.

In one example, each colorant member can be configured as a solid member such as a bar, pellet, briquette or the like. The solid member can include a granulated dye that is compressed with a binder (e.g., starch) to form the desired shape. The solid member can formulated to release the colorant when exposed to a body fluid for up to 2 or 3 months.

In one embodiment, the colorant member can include a substantially "V" shaped protrusion on the tissue-contacting surface. The "V" shaped protrusion can have the point arranged toward a surgical site, and the tip of the "V" can be used as a probe to make sure that the colorant is in contact with the surgical site. Often, surgical sites can have an indentation between ligated tissue portions as shown in FIG. 1D, and the colorant can include the "V" shape to point down into the indentation. The "V" shaped protrusion can function to provide a seal to the surgical site so that the colorant member directly receives any leakage from the surgical site. The "V" protrusion can also enhance contact between the colorant member and the surgical site so that any leakage can be detected quicker.

The colorant can be any biocompatible colorant. Some examples can include food dyes, such as brilliant blue FCF and indigotine blue, which are FDA approved. The colorant may also be a dye such as Trypan Blue.

In one embodiment, the colorant members can be glued to the resilient member with an adhesive. Any adhesive that is suitable for bonding with the materials of the resilient member and colorant members can be used. For example, silicone adhesives can be suitable.

FIG. 5A includes a perspective view of a leaf spring resilient member 500 of a leakage detecting implant, arranged in accordance with at least some embodiments described herein. The resilient member 500 includes a body 502 having pair of lateral wings 558 that function as spring flanges on each side of a "U" shaped center leaf spring 504. The "U" shaped center leaf spring 504 can include one or more holes 556; however the "U" shaped center leaf spring 504 may also be devoid of any holes in some embodiments. When the holes 556 are included, the colorant members can include a fastener member (see FIG. 4A) that is received through the holes 556 so as to couple the resilient member 500 with the colorant members. When devoid of the holes 556, the resilient member 500 can provide a compressive coupling that pushes on the colorant members as described herein. The "U" shaped center leaf spring 504 can include a convex inner surface 552 and a concave outer surface 554, which can facilitate the function of the resilient member 500 as a leaf spring.

The resilient member 500 can also include one or more circumferential supports 560 that can provide structural strength to the resilient member 500. As shown, the circumferential supports 560 can be located at the intersection of the "U" shaped center leaf spring 504 and lateral wings 558. Additionally, the resilient member 500 can include one or more lateral supports 562 as shown. The lateral supports 562 can extend across the "U" shaped center leaf spring 504, between the lateral wings 558, or between the circumferential supports 560. The resilient member 500 can have any number of lateral supports 562, such as one between each of the holes 556. The lateral supports 562 can facilitate the leaf spring function and enhance the resiliency of the resilient member 500.

FIG. 5B includes a cross-sectional view of a portion of the leaf spring resilient member 500 of FIG. 5A, arranged in accordance with at least some embodiments described herein. FIG. 5C includes a front profile view of the leaf spring resilient member 500 of FIG. 5A, arranged in accordance with at least some embodiments described herein.

FIG. 6A includes a perspective view of a torus resilient member 600 of a leakage detecting implant, arranged in accordance with at least some embodiments described herein. The torus resilient member 600 includes a body 602 having a circular cross-sectional profile in a ring shape that has a convex inner surface 604 and convex outer surface 606. However, the cross-sectional profile can be oval or elliptical. The torus resilient member 600 can have the body 602 in the shape of an o-ring, which is filled or hollow. The torus resilient member 600 can be prepared from a material, such as an elastomer, that provides the resilient functionality so that it functions as a spring. When the torus resilient member 600 is pressed from the inner surface 604 and/or outer surface 606 to a strained state, the resilient member 600 attempts to move to the relaxed state that has a substantially circular cross-sectional profile. When the torus resilient member 600 is trending from the compressed strained state in the implant, it provides the pressure to the colorant members as described herein.

FIG. 6B includes a cutaway view of the torus resilient member 600 of FIG. 6A, arranged in accordance with at least some embodiments described herein. The torus resilient member 600 is shown to be filled with a resilient material. However, it may also be hollow and tubular.

In one embodiment, the resilient member, as leaf spring or torus, can include one or more apertures that receive a portion of each of the biodegradable colorant members therethrough. While the leaf spring resilient member 500 is shown with the apertures (e.g., holes 556), the torus resilient member 600 may also include such apertures. Also, either of these resilient member configurations can be devoid of these apertures, where compressive coupling or adhesive can couple the resilient member with the colorant members.

In one embodiment, the resilient member includes a cross-sectional profile with a central arcuate portion (e.g., "U" shaped leaf spring) and a lateral resilient flange (e.g., lateral wing) on each side of the arcuate portion. The lateral resilient flanges can be coupled to the inner surface of the internal chamber of the cover member. Such a coupling can be by a fastener, adhesive, compression, or friction.

In one embodiment, the resilient member can include any suitable shape that is compatible with the shape of the cover member as described herein. Accordingly, the resilient member can be straight, rolled, coiled, annular, a portion of a ring shape, a "C" shape, and other shapes.

In one embodiment, the resilient member can be in a strained state before, during, and/or after implantation such that the resilient member attempts to trend to the relaxed state. The resilient member can be in the strained state (e.g., compressed state for torus or stretched state for a leaf spring) that exerts a force on the inner surface of the internal chamber of the cover member and on the colorant members. Accordingly, the resilient member can be resilient and have some shape memory so that the resilient member can be strained when in the implant and trend toward the natural or un-strained state as it presses the colorant member against tissue when implanted. Thus, the resilient member can change from a strained state toward a relaxed or natural state as the colorant members degrade after implantation.

In one embodiment, the resilient member can be biodegradable so that the implant does not need to be surgically removed. However, the biodegradation rate of the resilient member can be slower than a biodegradation rate of the biodegradable colorant members. This allows for the colorant members to degrade before the resilient member degrades so that the implant can function for leakage detection until the colorant is dissolved.

In one embodiment, the resilient member can be made of a polymer, such as an elastomer. Also, the resilient member can be made from a material having a complete degradation rate selected from polydioxanone (e.g., about 6 months until complete degradation), polycaprolactone (e.g., about 23-36 months until complete degradation), polyglycolide (e.g., about 6-12 months until complete degradation), polyglycolic acid (e.g., about 6-12 months until complete degradation), polylactide (e.g., about 1-12 months until complete degradation), polylactic acid (e.g., about 1-12 months until complete degradation), poly(lactic-co-glycolic acid), poly(glycolide-co-trimethylene carbonate) (e.g., about 6-12 months until complete degradation), polyhydroxybutyrate (e.g., complete degradation highly variable with cross-linking), POLYOX (e.g., variable time of months until complete degradation), Uriprene (e.g., variable months until complete degradation), magnesium alloy, magnesium-zinc-calcium alloy, magnesium-zinc-yttrium-neodymium alloy, or combinations or derivatives thereof.

The resilient member can have various shapes and sizes in accordance with the functionality described herein. The size can be modified depending on the organ or body lumen to receive the implant. In one aspect, a colon implant with a leaf spring resilient member can include a wall thickness of about 10 microns to about 1 mm, from about 50 microns to about 500 microns, from about 75 microns to about 250 microns, or from about 100 microns (i.e., 0.1 mm) to about 200 microns (i.e., 0.2 mm). The resilient member can also include a width or other dimension that is from about 1 mm to about 75 mm, from about 5 mm to about 50 mm, from about 10 mm to about 30 mm, or about 18 to about 22 mm. In one aspect, the annular resilient member can have an average diameter of about 25 mm to about 100 mm, from about 30 mm to about 75 mm, from about 40 mm to about 60 mm, or from about 45 mm to about 52 mm. However, the size can vary depending on whether the implant is for an infant, child, adolescent, teen, or adult. The sizing can also depend on the organ or body lumen to receive the implant.

In one example, the resilient member can be prepared from a biodegradable polymer and have the following dimensions: a thickness from 0.2 mm to about 0.5 mm; a width of about 10 mm to about 15 mm; and a diameter of about 48 mm to 52 mm.

The resilient member can be contoured sufficiently to have a spring-like property similar to a leaf spring. The flexibility or resiliency can be configured such that the resilient member can generate pressure to press the colorant member into the tissue to a depth of about 2 mm.

In one embodiment, the resilient member is integral with the cover member. That is, the cover member can include an internal bod portion in the internal chamber that functions as the resilient member. Accordingly, the cover member can be formed to have a body that also is the body for the resilient member.

In one embodiment, the resilient member can be formed from a pipe, which can be formed into a ring as a torus shape, or it can be cut in order to prepare the leaf spring shape. The leaf spring resilient member can include the "U" shaped center leaf spring that is formed by a round punch into a tube, and then cut to form the "M" shape as illustrated herein. The holes on in the "U" shaped center leaf spring portion can be manufactured by any hole punching operation.

The width of resilient member can be decided by considering the area that will receive the implant. As such, the size of the implant and individual components can be determined by the size of the anatomy at the surgical site. For anastomosis, the average colon thickness is about 2 mm to 3 mm, and the width of the resilient member can be 18-22 mm. The diameter of the resilient member can be determined by considering the diameter of colon at the surgical area. The average diameter of the colon is about 40 mm to 50 mm, which can be the inner diameter of the cover member, which results in the resilient member having a diameter of about 45-50 mm.

FIG. 7A includes a cross-sectional view of a cover member 700a of a leakage detecting implant, arranged in accordance with at least some embodiments described herein. The cover member 700a can include a body 702a having an outer surface 704a, an internal chamber 706a defined by an inner surface 708a, and affixation flanges 710a. The body 702a is shown to be arcuate or curved, but can also be squared, rectangular, or other shape, where the internal chamber 706a can match the shape of the body 702a. The fixation flanges 710a can be integrated with the main body 702a or be separate members that are coupled thereto. The fixation flanges 710a can extend from opposite ends 714a, 714b of the body 702a toward the opening 716a in the body 702a. The opening 716a is dimensioned to receive the colorant members therethrough.

FIG. 7B includes a cross-sectional view of a cover member 700b of a leakage detecting implant that has friction members 712 for retaining the colorant members, arranged in accordance with at least some embodiments described herein. The cover member 700b can include a body 702b having an outer surface 704b, an internal chamber 706b defined by an inner surface 708b, affixation flanges 710b, and friction members 712. The body 702b is shown to be arcuate or curved, but can also be squared, rectangular, or other shape, where the internal chamber 706b can match the shape of the body 702b. The affixation flanges 710b can be integrated with the main body 702b or be separate members that are coupled thereto. The fixation flanges 710b can extend from opposite ends 714a, 714b of the body 702b toward the opening 716b in the body 702b. The friction members 712 can extend from the ends 718a, 718b of the fixation flanges 710b into the internal chamber 706b. Optionally, the cover member 700b can include the friction members 712 terminating at a point at the inner surface 708b. As shown, friction strut members 722 can extend from the friction members 712 to the inner surface 708b. The friction members 712 and friction strut members 722 can be walls of the cover member, walls integrated with the cover member, or walls coupled to the cover member.

FIG. 7C includes a cross-sectional view of a cover member 700c of a leakage detecting implant having tissue affixation flanges 710c, arranged in accordance with at least some embodiments described herein. The cover member 700c can include a body 702c having an outer surface 704c, an internal chamber 706c defined by an inner surface 708c, and protruding affixation flanges 710c. The protruding affixation flanges 710c can have a wide dimension that extends past the opposite ends 714a, 714b of the body 702c and away from the opening 716c. The wide dimension can facilitate affixation to tissue as the size can enhance the ability to use adhesive, suture, or staples for affixing the implant to the tissue.

In one embodiment, the cover member can have a cross-sectional profile that is arcuate from one tissue-affixing surface to the other affixing surface. For example, the cover member can have a cross-sectional profile having substantially a "D" shape with the opening on the flat side. The one or more affixation surfaces can be oriented toward each other, which can be toward the opening in the cover member and toward the colorant members. The distance between the affixation surfaces can define the size of the opening in the cover member. Also, the size of the affixation surfaces can be configured so that they touch and provide friction to the colorant members protruding from the opening in the cover member.

The cover member can be configured with a rigidity or resiliency that is sufficient to withstand the pressure from the resilient member without substantially deforming the cover member and such that the resilient member can function as described herein. As such, the cover member can be rigid or a harder resiliency compared to the resilient member. That is, the cover member can be flexibly resilient and having a higher resiliency to deformation than the resilient member.

In one embodiment, the cover member can include any suitable shape that is compatible with the shape of the resilient member as described herein. As such, the cover member and resilient member can have the same shape. Accordingly, the cover member can be straight, rolled, coiled, annular, a portion of a ring shape, a "C" shape, and other shapes.

In one embodiment, the cover member can be biodegradable. Accordingly, the entire implant can be biodegradable.

However, the cover member can be configured to be biodegradable with a biodegradation rate that is slower than a biodegradation rate of the one or more colorant members. This can allow for the cover member to retain its structural integrity until after the colorant members have all degraded. Also, the biodegradation rate of the cover member can be the slower, the same, or faster than the resilient member.

In one embodiment, the cover member can be made of a polymer, such as an elastomer that is harder or has more resiliency than the resilient member. In fact, the cover member can be made of the same polymer as the resilient member that is configured to be harder or have more resiliency. For example, the cover member can be prepared from a material selected from polydioxanone (e.g., about 6 months until complete degradation), polycaprolactone (e.g., about 23-36 months until complete degradation), polyglycolide (e.g., about 6-12 months until complete degradation), polyglycolic acid (e.g., about 6-12 months until complete degradation), polylactide (e.g., about 1-12 months until complete degradation), polylactic acid (e.g., about 1-12 months until complete degradation), poly(lactic-co-glycolic acid), poly(glycolide-co-trimethylene carbonate) (e.g., about 6-12 months until complete degradation), polyhydroxybutyrate (e.g., complete degradation highly variable with cross-linking), POLYOX (e.g., variable time of months until complete degradation), Uriprene (e.g., variable months until complete degradation), magnesium alloy, magnesium-zinc-calcium alloy, magnesium-zinc-yttrium-neodymium alloy, or combinations or derivatives thereof. In some instances, the cover member and resilient member can be made of the same material.

The cover member can be made to be resiliently flexible or rigid. If the cover member is rigid, it can be made by regular injection molding process. The rigid cover member can be placed and/or positioned over the surgical site by suturing, stapling or adhesive. If the cover member is resiliently flexible, it can be made by an elastomeric process, and it can be placed and/or positioned over the surgical site with the implant applying some non-invasive pressure to the tissue around the surgical site. The resiliently flexible configuration allows the implant to be stretched when it is being placed at the surgical site.

The cover member can have various shapes and sizes in accordance with the functionality described herein. The size can be modified depending on the organ or body lumen to receive the implant. The cover member can include a dimension from the one or more affixing surfaces through the internal chamber to an outer surface of 0.5 mm to about 25 mm, from about 1 mm to about 15 mm, from about 1.5 mm to about 10 mm, or from about 2 mm to about 5 mm. The cover member can include a wall thickness of at least about 0.5 mm, or from about 0.25 mm to about 1 mm, from about 0.5 mm to about 0.75 mm, or about 0.5 mm. The cover member can include a width of about 15 mm to about 50 mm, from about 20 mm to about 40 mm, or from about 20 mm to about 25 mm. In one aspect, the annular cover member can have an average outer diameter of about 30 mm to about 110 mm, from about 35 mm to about 85 mm, from about 40 mm to about 65 mm, or from about 50 mm to about 55 mm. In one aspect, the annular cover member can have an average inner diameter (e.g., from affixation surface to affixation surface) of about 20 mm to about 90 mm, from about 25 mm to about 65 mm, from about 30 mm to about 55 mm, or from about 45 mm to about 50 mm. However, the size can vary depending on whether the implant is for an infant, child, adolescent, teen, or adult. The sizing can also depend on the organ or body lumen to receive the implant.

In one example, the cover member can include the following dimensions: the thickness from the affixation surfaces to the opposite surface it its peak can be from 2 mm to 5 mm; the thickness of the body can be from 0.5 mm to 0.7 mm; the inner diameter at the affixation surfaces can be from 45 mm to about 50 mm; the outer diameter from peak to peak can be from about 50 mm to about 55 mm; the width from side to side can be about 20 mm to about 25 mm. Of course sizes can be modified based on anatomy sizes. For example, the outer diameter of the cover member can be from about 25 mm to about 30 mm.

In one embodiment, the inner chamber can be filled with a material such as foam, gel, or other malleable material.

Figure 8B:
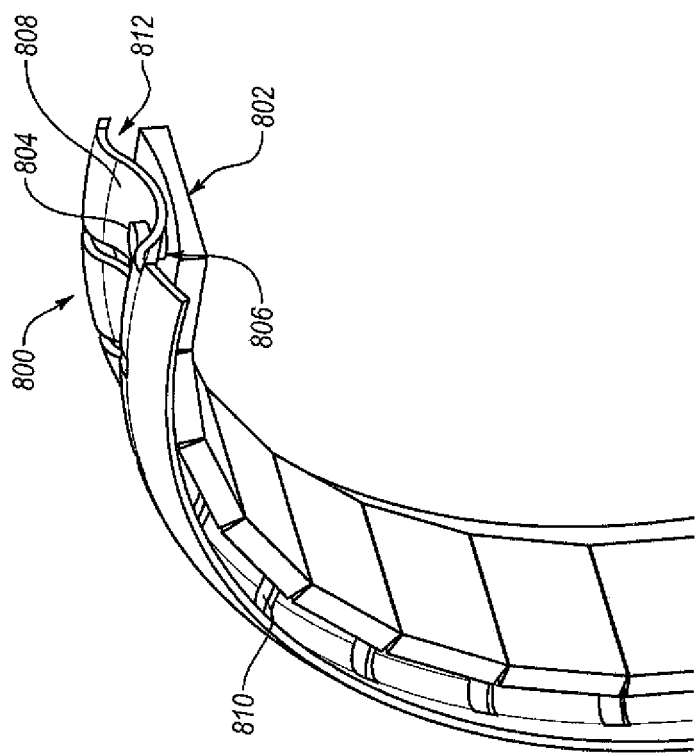
FIG. 8B includes a cutaway perspective view of the leaf spring resilient member coupled to colorant members of FIG. 8A.
Figure 8A:
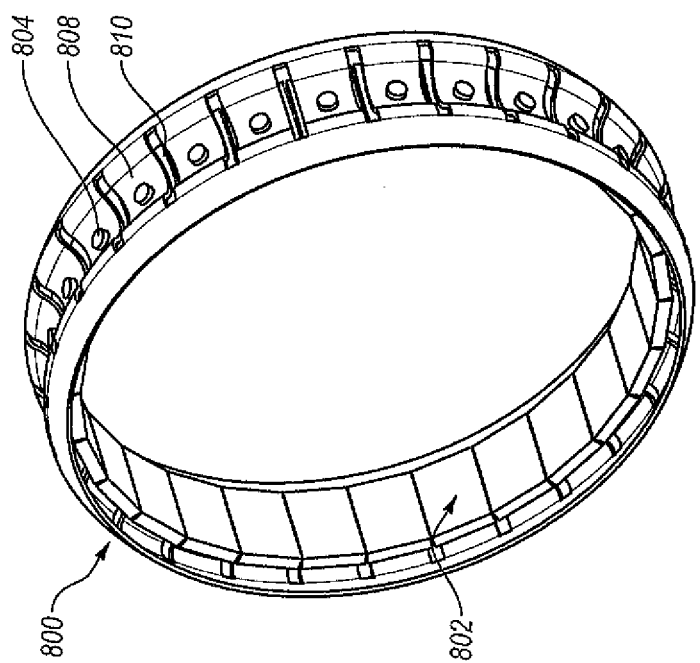
FIG. 8A includes a perspective view of a leaf spring resilient member coupled to colorant members.

FIG. 8A includes a perspective view of a leaf spring resilient member 800 coupled to colorant members 802, and FIG. 8B includes a cutaway perspective view of the leaf spring resilient member 800 coupled to colorant members 802 of FIG. 8A, both arranged in accordance with at least some embodiments described herein. The leaf spring resilient member 800 and colorant members 802 can be configured as illustrated and described in connection to FIGS. 1D and 5A. As shown, the colorant members 802 include a protrusion 804 that is inserted through a hole 806 in the resilient member 800. The resilient member 800 can be partitioned into sections 808 by lateral support members 810. Additionally, FIG. 8B shows an end 812 of the resilient member 800 if shaped as a portion of a ring or "C" shaped.

In one embodiment, the lateral support members 810 can be gaps or spaces that are cut out between the sections 808. The gaps instead of lateral support members 810 can increase the flexibility of the resilient member.

In one embodiment, the protrusion 804 can be a cylinder that has a size that is friction fit with the size of the hole 806.

FIG. 9A includes a cutaway perspective view of a flat leakage detecting implant 900*a* having a leaf spring resilient member 902*a*, arranged in accordance with at least some embodiments described herein. The implant 900*a* is shown to be flat so that it can be used at any surgical site. Also, the implant 900*a* can be rolled up or coiled for storage prior to use. This can allow for the implant 900*a* to be unrolled or uncoiled to the length needed, and then cut to size. The implant 900*a* can then be placed on the surgical site. This configuration also still allows for the implant 900*a* to be wrapped around an organ or body lumen, such as the colon. The cut end 910*a* can be sealed with an adhesive or plug member that fits in the end. The implant 900*a* is also shown to have a gap 904*a* between the colorant member 906*a* and the affixation flanges 908*a*.

FIG. 9B includes a cutaway perspective view of a flat leakage detecting implant 900*b* having a torus resilient member 902*b*, arranged in accordance with at least some embodiments described herein. The implant 900*b* is shown to be flat so that it can be used at any surgical site. Also, the implant 900*b* can be rolled up or coiled. This can allow for the implant 900*b* to be unrolled or uncoiled to the length needed, and then cut to size. The implant 900*b* can then be placed on the surgical site. This configuration also still allows for the implant 900*b* to be wrapped around an organ or body lumen, such as the colon. The cut end 910*b* can be sealed with an adhesive or plug member that fits in the end. The implant 900*a* is also shown to wide affixation flanges 912.

FIG. 9C includes schematic representations of side profiles of leakage detecting implants 950, 952, 954, arranged in accordance with at least some embodiments described herein. Implant 950 has an annular side profile. Implant 952 has a flat side profile. Implant 954 has a "C" shaped side profile. However, other side profile shapes can be used. Also, the implant can be flexible so that it can be bent into any side profile shape needed.

As described herein, the leakage detecting implant can be used in methods for detecting leaks from internal surgical sites. That is, the implant can be implanted on an internal surgical site, and release colorant if the internal surgical site leaks. The colorant can be visualized with the naked eye or with imaging equipment depending on the organ or body lumen that receives the implant.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Figure 10:
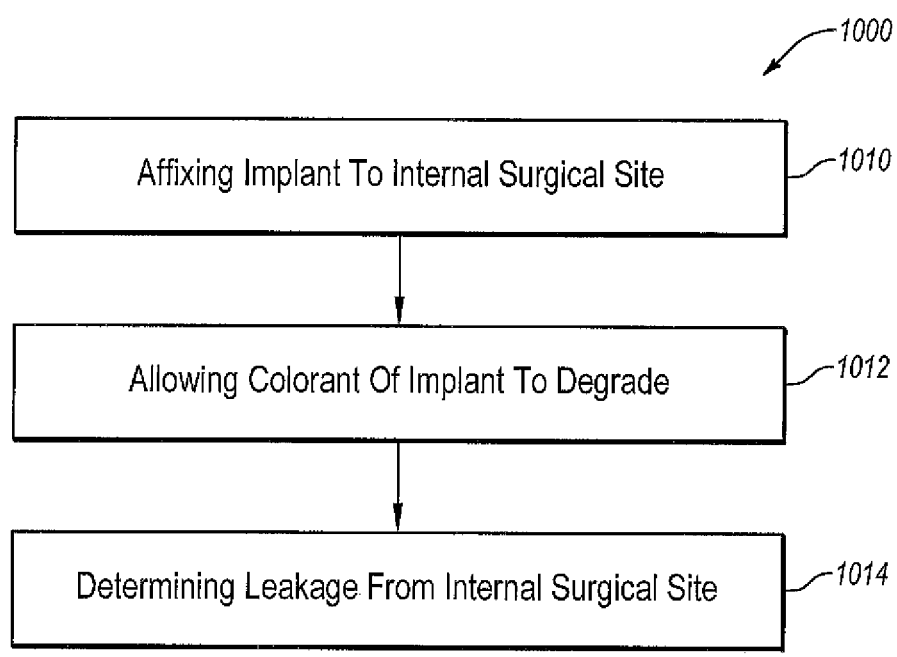
FIG. 10 includes a flow diagram of a method for detecting leakage from an internal surgical site.

FIG. 10 includes a flow diagram that describes a method 1000 for detecting leakage from an internal surgical site. The method 1000 can include the following: "Affixing Implant To Internal Surgical Site" (block 1010); "Allowing Colorant Of Implant To Degrade" (block 1012); and "Determining Leakage From Internal Surgical Site" (block 1014). Accordingly, the method 1000 can be initiated during a surgical procedure so that the implant can be affixed to the internal surgical site before an external surgical site or the skin is closed. After the internal surgical site is closed, a medical professional can affix an implant having one or more biodegradable colorant members to the internal surgical site in a subject ("Affixing Implant To Internal Surgical Site" block 1010). After the end of the surgical procedure, the implant is left at the internal surgical site so as to allow the biodegradable colorant to degrade at the internal surgical site ("Allowing Colorant Of Implant To Degrade" block 1012). After the implant is left on the internal surgical site, the surgical site may or may not bleed or ooze other body fluids. When the internal surgical site is intact, no blood or other body fluid will contact the biodegradable colorant member, and the colorant member will not degrade and release the colorant. When the internal surgical site has a leakage, blood or other body fluid will contact the colorant and degrade the colorant member so that the colorant is released. Accordingly, when the implant is on the GI tract, the patient can check their stool color in order to determine whether color of the colorant member is leaking from the surgical site ("Determining Leakage From Internal Surgical Site" block 1014). The colorant can be visualized with the naked eye or with imaging equipment. For example, when the surgical site is at the GI tract, such as at the colon, the visualization can be with the naked eye. In another example, when the surgical site is on another organ, such as the liver or kidney, the colorant can be visualized with imaging equipment which can be facilitated by the colorant being radiopaque.

In one embodiment, the method can include providing or preparing the implant for use. The implant can be provided ready to use in various shapes or configurations. Also, a roll or coil of the implant can be provided, and implant can be cut and prepared therefrom. When cut, the implant cut end can be sealed with an adhesive, plug, or the like. The implant can also be provided with a releasable liner on the colorant members, where the liner is removed prior to implantation. A degradable liner can be left on the colorant members.

In one embodiment, the method can include affixing one or more affixation surfaces of the implant to tissue of an organ or body lumen adjacent to the surgical site with adhesive, sutures, or staples. However, any other method of affixation of the implant to the tissue can be used. The adhesive can be surgical adhesive, such as a cyanoacrylate. Standard surgical sutures or staples can be used. The affixation can be performed by affixing the affixation surfaces described herein to the tissue so that the colorant members contact the surgical site. Also, the affixation can include placement of the implant so that the colorant members cover the surgical site and extend over tissue adjacent to the surgical site. The affixation can be sufficient to seal the cover member on the tissue.

In one embodiment, the method can include allowing the resilient member to apply pressure to the one or more biodegradable colorant members so as to apply pressure to the surgical site. The pressure can be generated by placing the resilient member in a strained state so that it pushes against the cover member and against the colorant member. Pushing the colorant member can also apply pressure to the surgical site, which can be beneficial to inhibit bleeding or oozing. As such, the implant can be used to improve the healing of the surgical site.

In one embodiment, the implant can be the shape of a continuous ring. Accordingly, the implant can be placed over the surgical site when the organ or body lumen is cut apart so that two ends are open. The implant can be slid over one end before the two ends are closed and ligated together. Such a method is now described in more detail.

Figure 11:
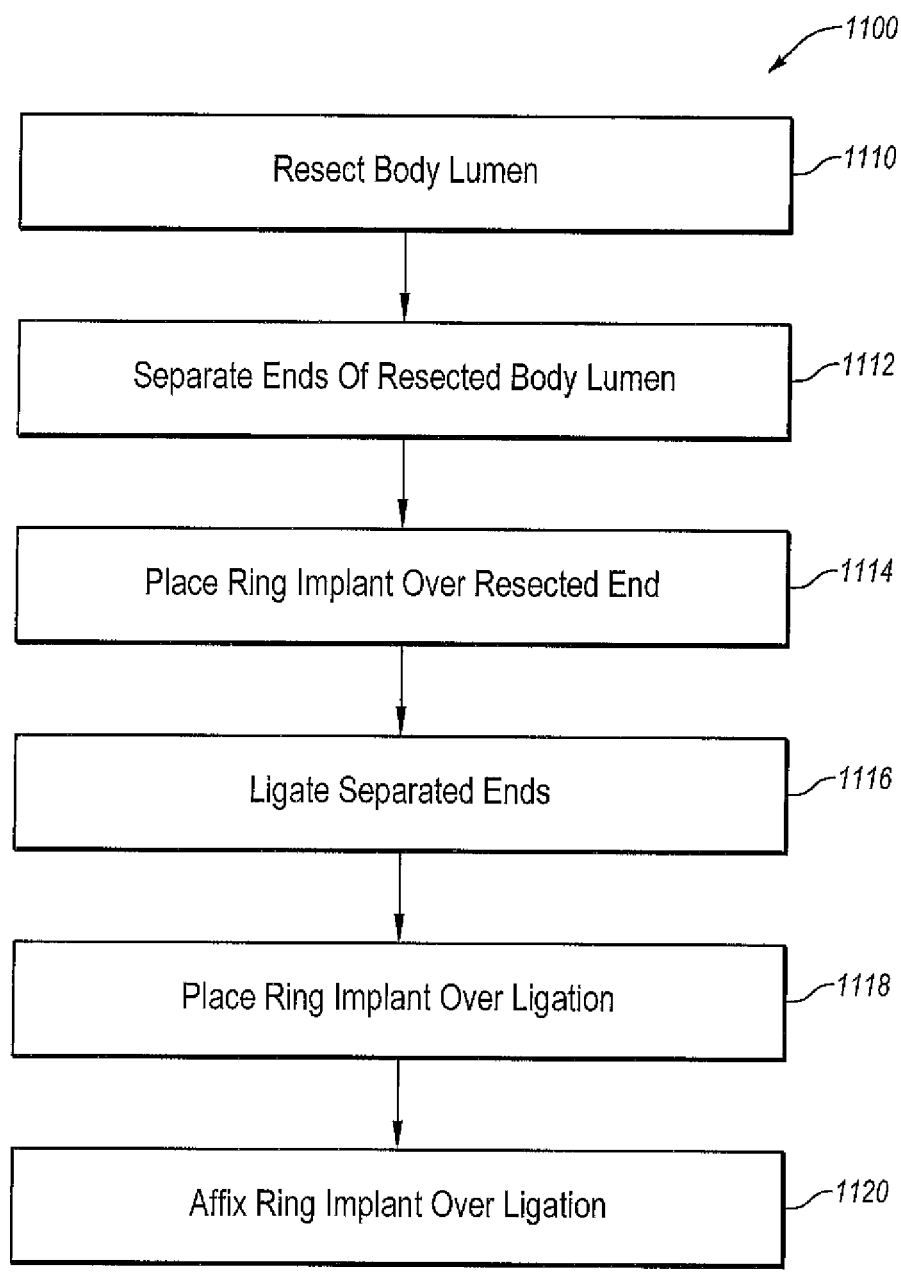
FIG. 11 includes a flow diagram of a method for detecting leakage from an internal surgical site of a resection.

FIG. 11 includes a flow diagram that describes a method 1100 for detecting leakage from an internal surgical site on a body lumen. The method 1100 can include the following: "Resect Body Lumen" (block 1110); "Separate Ends Of Resected Body Lumen" (block 1112); "Place Ring Implant Over Resected End" (block 1114); "Ligate Separated Ends" (block 1116); "Place Ring Implant Over Ligation" (block 1118); and "Affix Ring Implant Over Ligation" (block 1120). A ring-shaped implant as described herein can be useful for detecting leakage from a resected body lumen, such as the colon. Accordingly, the method can include performing a surgical procedure to produce the surgical site, where the surgical procedure includes resecting a portion of a GI tract of a subject ("Resect Body Lumen" block 1110). Resections that slice a body lumen into two separate segments are common surgical procedures, and can include a colon anastomosis. While the body organ is resected so that two ends are open, the ring-shaped implant can be implanted. After the body lumen is sliced, the medical professional can attend to separating a first portion of the GI tract from a second portion ("Separate Ends Of Resected Body Lumen" block 1112). Generally, the two portions can be pulled away from each other to expose the two cut ends. The medical professional can then place the implant on the resected body lumen. This can include placing the ring implant over one of the first or second portions ("Place Ring Implant Over Resected End" block 1114). Once the ring is fit over one of the cut ends, it can be slid over the body lumen so that the cut ends can be reconnected. Accordingly, the medical professional can attend to ligating the first portion with the second portion, wherein the surgical site includes the ligation ("Ligate Separated Ends" block 1116). The ligation can be performed in any manner that is commonly used or later developed. However, the ligation should reconnect the cut ends sufficiently, which may include the use of bioadhesive (e.g., cyanoacrylate), sutures, or staples. The ligation forms the surgical site that may be prone to leakage. After ligation, the medical professional can slid the ring implant over the ligation site. This can include placing the ring implant at the surgical site so that a portion of ring implant is at the first portion of the GI tract and a portion of the ring implant is at the second portion of the GI tract ("Place Ring Implant Over Ligation" block 1118). Once the ring implant is the proper position, it can be fixed in place. The medical professional can attend to affixing the implant to the first portion and second portion of the GI tract such that the one or more biodegradable colorant members contact the ligation ("Affix Ring Implant Over Ligation" block 1120). The implant can be affixed by bioadhesive, sutures, or staples. Also, a resiliently flexible implant may be stretched during placement so that pressure holds the implant in place.

After the implant is in place and the surgical procedure is finished, the implant can be monitored to determine if the colorant members degrade and release the colorant. When implanted in a body anywhere besides the GI tract, x-ray, fluoroscopy, or other technique can be used to monitor leakage from the surgical site. When the implant is implanted on the GI tract, leakage detection can include monitoring stool color of the subject after implantation of the implant. The observation of stool color can be done by the patient of the surgical procedure in a medical environment or in the comfort of their own home.

In one embodiment, the method of detecting leakage can include observing stool of the subject to include color of the colorant members. When stool color includes the color of the colorant members the surgical site is leaking. Otherwise, observing stool of the subject that is devoid of color of the colorant members can indicate that the stool is devoid of the color of the colorant members, and it can be determined that the surgical site is not leaking.

In one embodiment, the colorant can be fluorescent, and the stool can be monitored using a UV light. In another embodiment, the colorant can be phosphorescent so that the stool can be illuminated with the appropriate light, and glowing stool can be observed in the dark. Often, phosphorescent materials appear fluorescent under UV light.

In one embodiment, the implant has a "C" shape. After a standard colorectal anastomotic is performed, the "C" shaped implant is positioned over the anastomosis site, and snapped and/or otherwise fitted around the anastomosis site. The "C" shaped implant is then sutured, stapled, or glued to the tissue of the colon in order to inhibit the implant form migrating.

In one embodiment, the implant has the shape of a closed ring. After the body organ is resected (e.g., cancerous tissue is removed), the ring implant is slide over the colon through the cut area (e.g. at the side upstream body part). Then the anastomosis is completed by suturing or by a linear stapler. After anastomosis of the surgical site, the ring implant is slide over the anastomosis site and sutured, stapled, or glued to the tissue of the colon in order to prevent the implant from migrating from the anastomosis. In one aspect, the suture can be a bioabsorbable suture.

In one embodiment, the leakage detecting implant can be manufactured to include the features and functionality as described herein. Such a manufacture can be by any suitable manufacturing protocol in order to produce an implant with the features and functionality as described herein.

Figure 12:
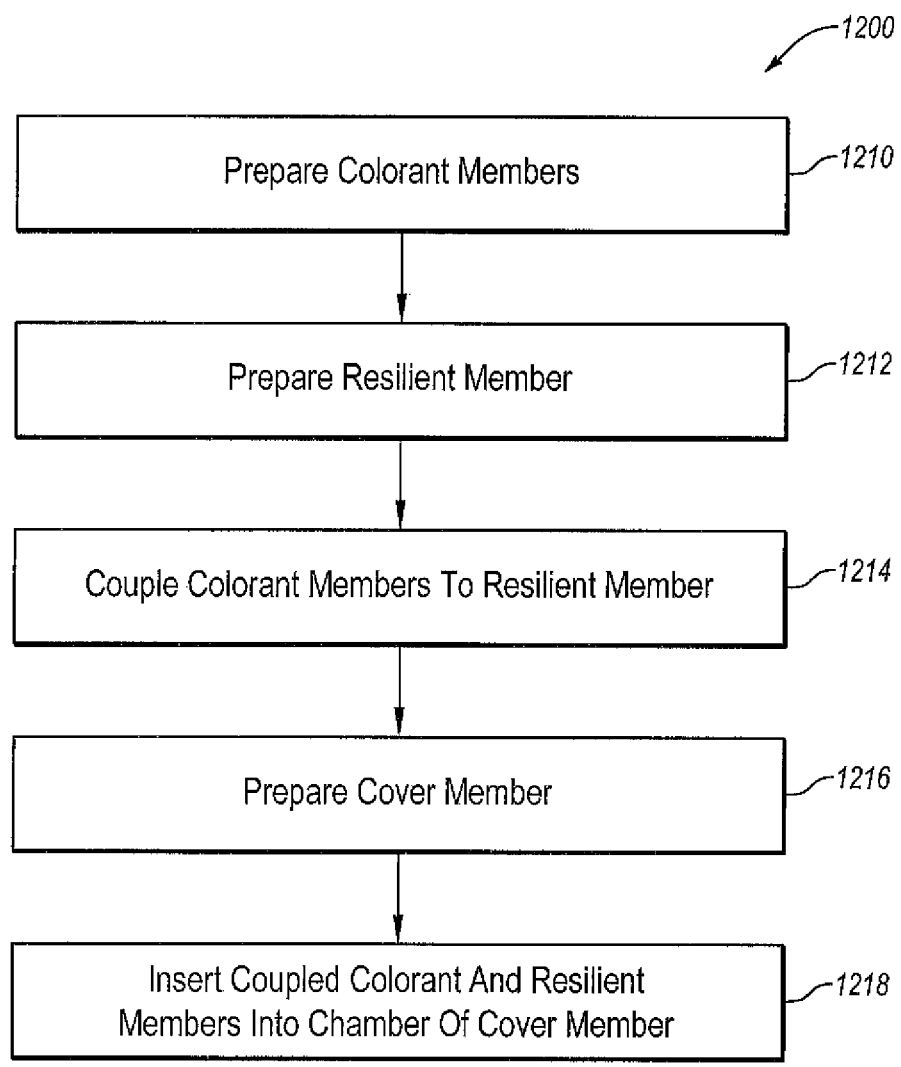
FIG. 12 includes a flow diagram of a method for manufacturing a leakage detecting implant, all arranged in accordance with at least some embodiments described herein.

FIG. 12 includes a flow diagram that describes a method 1200 of manufacturing an implant. The manufacturing method 1200 can include the following: "Prepare Colorant Members" (block 1210); "Prepare Resilient Member" (block 1212); "Couple Colorant Members To Resilient Member" (block 1214); "Prepare Cover Member" (block 1216); and "Insert Coupled Colorant And Resilient Members Into Chamber Of Cover Member" (block 1218). Manufacturing the implant can include preparing each of the components, and then coupling the components together in order to prepare the implant to include the features and functionality as described herein. As such, the method of manufacture can include preparing one or more biodegradable colorant members having a tissue-contacting inner surface and an opposite outer surface ("Prepare Colorant Members" block 1210). The colorant members can be prepared by any manner suitable for preparation of the embodiment of the colorant member being used. For example, colorant powder can be pressed with a binder into a briquette, or the powder can be included in a degradable package. Also, the colorant can be absorbed into a paper or other medium that can degrade. The resilient member in the leaf spring or torus embodiments can be prepared by any manner suitable, such as injection molding, extrusion, or the like. ("Prepare Resilient Member" block 1212). The colorant members and resilient member can be coupled together, such as by coupling the inner surface of the resilient member to the outer surface of the biodegradable colorant members ("Couple Colorant Members To Resilient Member" block 1214). The cover member can be prepared to include a body with an internal chamber and an opening on a tissue-contacting side between one or more affixation surfaces adapted to be affixed to tissue of a subject ("Prepare Cover Member" block 1216). Once all of the components have been prepared, the implant can be assembled. Assembly of the implant can include inserting the coupled resilient member and biodegradable colorant members into the internal chamber of the cover member ("Insert Coupled Colorant And Resilient Members Into Chamber Of Cover Member" block 1218). The assembly can be performed such that the internal chamber contains the resilient member and at least a portion of the one of each of the biodegradable colorant members. One or more of the colorant members can have the tissue-contacting inner surface exposed through the opening of the cover member. The cover member can have an inner surface of the internal chamber coupled to an outer surface of the resilient member. It should be noted that the colorant members and resilient member can be coupled together before, during or after being inserted into the internal chamber of the cover member. For example, the resilient member can be inserted into the cover member before being coupled to the colorant members.

In one embodiment, the manufacture process can include preparing each biodegradable colorant member to have a biocompatible colorant. The colorant members can be formed into biodegradable solids, biodegradable aggregated particles, colored sheets, colored papers, sustained release members, biodegradable shell and colorant core members, and liquids or gels or powders in a biodegradable package as well as other suitable forms.

In one embodiment, the biodegradable colorant members can be prepared to include a fastener member. The fastener member can be configured with fastener features sufficient to couple the colorant members with the resilient member. For example, coupling the colorant member with the resilient member can include inserting the fastener member into or through the resilient member so as to couple the one or more biodegradable colorant members to the resilient member. As such, the resilient member can be manufactured include a hole or aperture adapted to receive the fastener member.

In one embodiment, the resilient member and cover member can be manufactured with compositions that are biodegradable. Both the resilient member and cover member can have a biodegradation rate that is slower than a biodegradation rate of the one or more biodegradable colorant members. The relative biodegradation rates of the cover member and resilient member can vary.

In one embodiment, the colorant members can be manufactured to include a plastic film. The film can be peelable or biodegradable. In any event, the film can be adhered with adhesive to the tissue-contacting surfaces of the colorant members.

In one embodiment, injection molding can be used to prepare the cover member and resilient member, compression molding can prepare the colorant members, and film extrusion can prepare the film before all of these parts are assembled into the implant. The film is stuck to the colorant member in a manner similar to sticking a sticker. The colorant having the film on one side is then coupled at the other side to the resilient member, such as a snap fit, hook fitting, or adhesive. The sub-assembly having the resilient member and colorant members is then placed into the internal cavity of the cover member. The sub-assembly can be retained in the internal chamber by the resilient member, or it can be fixed by being snap fitted, welded, or adhered to the inner surface of the internal chamber.

In one embodiment, the implant can be manufactured to have a flat structure, such as a snap band, flat plate, or the like. Also, the implant can be prepared to be flexibly resilient similar to an elastic band. Also, the implant can be prepared to be flexible like a cloth so that it can be rolled on the anastomosis site, and then affixed to the colon surface.

In one embodiment, the implant can be a ring that has break that allows it to open into a "C" shape during implantation and the reform the ring after implantation. Accordingly, the ring implant can be configured similar to a bracelet that can open during the implantation, and then closed back to the ring shape around the colon or other organ.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods or embodiments, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety.

The invention claimed is:

1. An internal leakage detecting implant for detecting leakage from an internal surgical site comprising:
    one or more biodegradable colorant members having a tissue-contacting inner surface and an opposite outer surface;
    a resilient member having an inner surface coupled to the outer surface of the one or more biodegradable colorant members; and
    a cover member having an elongate fluid-impermeable body with an internal chamber and an opening on a tissue-contacting side adapted to be placed over an internal surgical site in a tissue, the internal chamber containing the resilient member and at least a portion of the one or more biodegradable colorant members with the tissue-contacting inner surface exposed through the opening, the cover member having an inner surface of the internal chamber coupled to an outer surface of the resilient member, the tissue-contacting side having one or more affixation surfaces adapted to be affixed to tissue of a subject, wherein the fluid-impermeable body provides a fluid-tight seal when the one or more affixation surfaces are affixed to the tissue so that the opening is over the internal surgical site in the tissue to exposed the one or more biodegradable colorant members to the internal surgical site.

2. The implant of claim 1, wherein the one or more biodegradable colorant members include a visible colorant, fluorescent colorant, phosphorescent colorant, radiopaque colorant, reactive colorant, device-detectable colorant, or combination thereof.

3. The implant of claim 1, wherein the one or more biodegradable colorant members include a fastener member that couples the one or more biodegradable colorant members with the resilient member.

4. The implant of claim 1, wherein the resilient member includes one or more apertures that receive a portion of the one or more biodegradable colorant members therethrough.

5. The implant of claim 1, wherein each of the resilient member and the cover member is biodegradable with a biodegradation rate that is slower than a biodegradation rate of the one or more biodegradable colorant members.

6. The implant of claim 1, wherein each of the resilient member and the cover member includes an arcuate or annular shape, and wherein the resilient member in a compressed state exerts a force on the inner surface of the internal chamber of the cover member and on the one or more biodegradable colorant members.

7. The implant of claim 1, wherein the cover member has a cross-sectional profile that is arcuate from a first affixation surface to a second affixation surface, where the first and second affixation surfaces are oriented toward each other.

8. The implant of claim 1, wherein the internal chamber of the elongate body of the cover member has a cross-sectional profile with a "D" shape.

9. The implant of claim 1, wherein the one or more biodegradable colorant members includes a blue colorant.

10. The implant of claim 1, wherein the tissue-contacting inner surface of the one or more biodegradable colorant members protrudes through the opening of the cover member.

11. The implant of claim 1, wherein the one or more affixing surfaces are formed from the body of the cover member.

12. The implant of claim 1, wherein the one or more affixing surfaces are a portion of the elongate body and at least partially define the internal chamber and opening on the tissue-contacting side of the cover member.

13. The implant of claim 1, wherein the one or more biodegradable colorant members comprises a fastener member with a protrusion, wherein the protrusion is configured to couple the one or more biodegradable colorant members to the resilient member when the protrusion is inserted into or through the resilient member.

14. The implant of claim 13, wherein the protrusion includes a hook, barb, tine, or stem and head.

15. The implant of claim 1, wherein the one or more biodegradable colorant members include at least about 0.4 g or 0.4 mL of colorant.

16. The implant of claim 1, wherein the one or more biodegradable colorant members include a volume of about 1 mL to about 2 mL.

17. The implant of claim 1, wherein the one or more biodegradable colorant members include:
    a thickness of about 100 microns to about 1 mm; and
    a width or diameter of about 8 mm to about 12 mm.

18. The implant of claim 1, wherein the resilient member includes a cross-sectional profile that is circular.

19. The implant of claim 1, wherein the resilient member is a hollow tube or filled tube.

20. The implant of claim 1, wherein the resilient member includes an arcuate cross-sectional profile.

21. The implant of claim 1, wherein the resilient member includes a cross-sectional profile with a central arcuate portion and a lateral resilient flange on each side of the arcuate portion, wherein the lateral resilient flanges are configured to coupl to the inner surface of the internal chamber of the cover member.

22. The implant of claim 1, wherein the resilient member includes a wall thickness of about 0.1 mm to about 0.2 mm and a width of about 18 mm to about 22 mm.

23. The implant of claim 1, wherein the resilient member is a ring having an average diameter of about 45 mm to about 52 mm.

24. The implant of claim 1, wherein the cover member includes a wall that extends from an end of the one or more affixation surfaces into the internal chamber of the cover member.

25. The implant of claim 1, wherein the cover member is rigid.

26. The implant of claim 1, wherein the cover member is flexibly resilient and has a higher resiliency to deformation than the resilient member.

27. The implant of claim 1, wherein the cover member has:
    a dimension from the one or more affixation surfaces to an outer surface of about 2 mm to about 5 mm;
    a wall thickness of at least about 0.5 mm; and
    a width of about 20 mm to about 25 mm.

28. The implant of claim 1, wherein the cover member comprises a ring shaped member that has an average inner diameter of about 45 mm to about 50 mm and an average outer diameter of about 50 mm to about 55 mm.

29. The implant of claim 1, further comprising a biodegradable film located on the tissue-contacting inner surface of the one or more biodegradable colorant members.

30. A method of detecting leakage from an internal surgical site, the method comprising: providing the implant of claim 1; affixing the implant having one or more biodegradable colorant members to tissue surrounding the internal surgical site in a subject so that the implant forms a fluid-tight seal with the tissue; allowing the one or more biodegradable colorant members to degrade at the surgical site; and determining whether color of the one or more colorant members is leaking through the surgical site.

31. The method of claim 30, wherein the implant includes a shape of a ring, the method comprising: performing a surgical procedure to produce the surgical site, the surgical procedure resecting a portion of a gastrointestinal tract of a subject, during the resection: separating a first portion of the gastrointestinal tract from a second portion; placing the ring implant over one of the first or second portion; ligating the first portion with the second portion, wherein the surgical site includes the ligation; placing the ring implant at the surgical site so that a portion of the ring implant is at the first portion of the gastrointestinal tract and a portion of the ring implant is at the second portion of the gastrointestinal tract, and wherein the opening of the cover member is at the surgical site; and affixing the implant to the first portion and second portion of the gastrointestinal tract such that the one or more biodegradable colorant members contact the ligation.

32. The method of claim 31, further comprising monitoring stool color of the subject after implantation of the implant.

33. The method of claim 32, further comprising observing stool of the subject to include color of the one or more biodegradable colorant members, when stool color includes the color of the one or more biodegradable colorant members the surgical site is leaking.

34. The method of claim 30, comprising affixing the one or more affixation surfaces of the implant to tissue of an organ adjacent to the surgical site with adhesive, sutures, or staples.

35. The method of claim 30, wherein the affixing of the implant to the tissue further comprises affixing the implant such that the resilient member applies pressure to the one or more biodegradable colorant members so that the one or more colorant members apply pressure to the surgical site.

36. A method of manufacturing the implant of claim 1, the method comprising:
  providing a cover member having an elongate body that is fluid-impermeable with an internal chamber and an opening on a tissue-contacting side, the cover member having an inner surface of the internal chamber, the tissue-contacting side having one or more affixation surfaces adapted to be affixed to tissue of a subject;
  inserting a resilient member through the opening and into the internal chamber of the cover member so that an outer surface of the resilient member presses against an inner surface of the internal chamber of the cover member and an inner surface of the resilient member is exposed through the opening; and
  inserting one or more biodegradable colorant members through the opening and into the internal chamber of the cover member so that an outer surface of the one or more biodegradable cover members presses against the inner surface of the resilient member, the one or more biodegradable colorant members having a tissue-contacting inner surface that is opposite of the outer surface, wherein the resilient member biases the one or more biodegradable colorant members through the opening of the cover member.

* * * * *

UNITED STATES PATENT AND TRADEMARK OFFICE
CERTIFICATE OF CORRECTION

PATENT NO.         : 9,636,065 B2                                   Page 1 of 1
APPLICATION NO.    : 14/350746
DATED              : May 2, 2017
INVENTOR(S)        : Borkar et al.

It is certified that error appears in the above-identified patent and that said Letters Patent is hereby corrected as shown below:

In the Claims

In Column 25, Line 37, in Claim 1, delete "exposed" and insert -- expose --, therefor.

In Column 26, Line 8, in Claim 11, delete "affixing" and insert -- affixation --, therefor.

In Column 26, Line 12, in Claim 12, delete "affixing" and insert -- affixation --, therefor.

In Column 26, Line 43, in Claim 21, delete "coupl to" and insert -- couple the --, therefor.

Signed and Sealed this
First Day of August, 2017

Joseph Matal
*Performing the Functions and Duties of the*
*Under Secretary of Commerce for Intellectual Property and*
*Director of the United States Patent and Trademark Office*